(12) United States Patent
Petrenko et al.

(10) Patent No.: US 6,630,345 B2
(45) Date of Patent: Oct. 7, 2003

(54) NUCLEIC ACIDS ENCODING A CALCIUM INDEPENDENT RECEPTOR OF α-LATROTOXIN, CHARACTERIZATION AND USES THEREOF

(75) Inventors: Alexandre G. Petrenko, Fair Lawn, NJ (US); Valery G. Krasnoperov, Brooklyn, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 08/811,519

(22) Filed: Mar. 4, 1997

(65) Prior Publication Data

US 2003/0143665 A1 Jul. 31, 2003

(51) Int. Cl.$^7$ ............... C12N 15/12; C12N 15/63; C12N 15/85
(52) U.S. Cl. ............. 435/325; 435/252.3; 435/320.1; 536/23.5
(58) Field of Search ............... 536/23.1, 23.5; 435/252.3, 325, 320.1

(56) References Cited

PUBLICATIONS

Sambrook et al "Molecular Cloning, A Laboratory Manual" Cold Spring Harbor Press, USA (1989) pp. 10.13.*
Lelianova et al., GenBank Accession No. U78105, 1996.*
Rudinger. In "Peptide Hormones" (ed. J.A. Parsons) University Park Press, Baltimore, pp. 1–7, 1976.*
Krasnoperov, V.G. et al. 1997, Database Genbank Accession No. U72487.1, LOCUS AAC53268.
Barbieri., 1994, in Basic Pharmacology in Medicine, Medical Surveillance, West Chester, PA , pp42–64.
Krasnoperov et al., 1997, Neuron, 18:925–37.
Lathe et al., 1985, J Mol Biol, 183:1–12.
Lelianova et al., 1997, J Biol Chem, 272:21504–8.
Malone, 1994, Database Genbank, Accssion No.: U 13852, XP 002066461.
Barnett et al., 1996 (in press).
Ceccarelli and Hurlbut, 1980, J. Cell Biol. 87, 297–303.
Clark et al., 1970, Nature 225, 703–705.
Davletov et al., (1996) *J. Biol Chem.* 271, 23239–23245.
Davletov et al., 1995, J. Biol. Chem. 270, 23903–23905.
Finkelstein et al., *Science* 193, 1009–1011 (1976).
Fritz et al., 1980, Nature 283, 486–487.
Frontali et al., 1976, J. Cell Biol. 68, 462–479.
Geppert et al., 1994, Cell 79, 717–727.
Gorio et al., 1978, J. Neurocytology 7, 193–202.
Grasso et al., *Nature* 283, 774–776 (1980).
Hamann et al. (1996) Genomics 32:144–7.
Hurlbut et al., *J. Membr. Biol.* 138, 91–102 (1994).
Hurlbut et al., 1990, J. Physiol.—London 425, 501–526.
Krasnoperov et al., (1996), *Biochem. Biophys. Res. Comm.*, 227:868–75.
Lishko et al., 1990, FEBS Lett. 266, 99–101.
McMahon et al., 1990, J. Neurochem. 55, 2039–2047.
Meldolesi et al., 1984, Proc. Natl. Acad. Sci. USA 81, 620–624.
Meldolesi et al., 1983, Neuroscience 10, 997–1009.
Meldolesi, *J. Neurochem.* (1982) 38, 1559–1569.
Misler and Hurlbut, 1979, Proc. Natl. Acad. Sci. USA 76, 991–995.
Nicholls et al., *Proc. Natl. Acad. Sci* USA 79, 7924–7928 (1982).
O'Connor et al. (1993) FEBS Lett. 326, 255–260.
Okamoto et al., 1971, Science 172, 733–736.
Parpura et al., 1995, FEBS Letters. 360, 266–70.
Petrenko et al., 1996, *J. Neurosci.* 16, 4360–4369.
Petrenko, *FEBS Lett.* 1993) 325, 81–85.
Petrenko et al. (1993) J. Biol. Chem. 268:1860–7.
Petrenko et al., 1991 Nature 353, 65–68.
Petrenko et al., (1990) EMBO J. 9, 2023–2027.
Puschel and Betz, *J. Neurosci.* (*1995*) 15, 2849–2856.
Robello et al., *J. Membr. Biol.* 95, 55–672 (1987).
Rosenthal et al., 1990, Mol. Pharmacol. 38, 917–923.
Rosenthal and Meldolesi, 1989, J. Pharmacol. Ther. 42, 115–134.
Rubin et al., 1978, Brain Res. 143, 107–124.
Scheer and Meldolesi, *EMBO J.* (1985) 4, 323–327.
Shoji–Kasai et al., 1994, FEBS Letters 353, 315–318.
Strader et al. (1994) Ann. Rev. Biochem. 63:101–32.
Tzeng and Siekevitz, *J. Neurochem.* (1979) 33, 263–274.
Tzeng et al., 1978, Proc. Natl. Acad. Sci. USA 75, 4016–4020.
Ushkaryov et al., *Science* (1992) 257, 50–56.
Vicentini et al., 1984, Biochem. Biophys. Res. Commun. 121, 538–544.
Wanke et al., *Biochem. Biophys. Res. Commun.* 134, 320–325 (1986).

* cited by examiner

*Primary Examiner*—Gary Kunz
*Assistant Examiner*—Robert C. Hayes
(74) *Attorney, Agent, or Firm*—Klauber & Jackson

(57) ABSTRACT

A novel receptor of α-latrotoxin (α-LTx) which binds α-LTx independently of calcium ($Ca^{2+}$) presence and is thus a mediator of the calcium-independent stimulation of neurotransmitter release by α-latrotoxin has been isolated, purified and characterized. Designated CIRL (calcium-independent receptor of α-latrotoxin), it and its endogenous ligands can be used to modulate and regulate spontaneous calcium-independent neurotransmitter release and produce α-latrotoxin-like effects on the nerve terminal.

8 Claims, 12 Drawing Sheets

FIG. 2A

```
MARLAAALWSLCVTTVLVTSATQGLSRAGLPFGLMRRELACEGYPIELRC      50
PGSDVIMVENANYGRTDDKICDADPFQMENVQCYLPDAFKIMSQRCNNRT     100
QCVVVAGSDAFPDPCPGTYKYLEVQYDCVPYKVEQKVFVCPGTLQKVLEP     150
TSTHESEHQSGAWCKDPLQAGDRIYVMPWIPYRTDTLTEYASWEDYVAAR     200
HTTTYRLPNRVDGTGFVVYDGAVFYNKERTRNIVKYDLRTRIKSGETVIN     250
TANYHDTSPYRWGGKTDIDLAVDENGLWVIYATEGNNGRLVVSQLNPYTL     300
RFEGTWETGYDKRSASNAFMVCGVLYVLRSVYVDDDSEAAGNRVDYAFNT     350
NANREEPVSLAFPNPYQFVSSVDYNPRDNQLYVWNNYFVVRYSLEFGPPD     400
PSAGPATSPPLSTTTTARPTPLTSTASPAATTPLRRAPLTTHPVGAINQL     450
GPDLPPATAPAPSTRRPPAPNLHVSPELFCEPREVRRVQWPATQQGMLVE     500
RPCPKGTRGIASFQCLPALGLWNPRGPDLSNCTSPWVNQVAQKIKSGENA     550
ANIASELARHTRGSIYAGDVSSSVKLMEQLLDILDAQLQALRPIERESAG     600
KNYNKMHKRERTCKDYIKAVVETVDNLLRPEALESWKDMNATEQVHTATM     650
LLDVLEEGAFLLADNVREPARFLAAKQNVVLEVTVLSTEGQVQELVFPQE     700
YASESSIQLSANTIKQNSRNGVVKVVFILYNNLGLFLSTENATVKLAGEA     750
GTGGPGGASLVVNSQVIAASINKESSRVFLMDPVIFTVAHLEAKNHFNAN     800
CSFWNYSERSMLGYWSTQGCRLVESNKTHTTCACSHLTNFAVLMAHREIY     850
QGRINELLLSVITWVGIVISLVCLAICISTFCFLRGLQTDRNTIHKNLCI     900
NLFLAELLFLVGIDKTQYEVACPIFAGLLHYFFLAAFSWLCLEGVHLYLL     950
LVEVFESEYSRTKYYYLGGYCFPALVVGIAAAIDYRSYGTEKACWLRVDN    1000
YFIWSFIGPVSFVIVVNLVFLMVTLHKMIRSSSVLKPDSSRLDNIKSWAL    1050
GAIALLFLLGLTWAFGLLFINKESVVMAYLFTTFNAFQGVFIFVFHCALQ    1100
KKVHKEYSKCLRHSYCCIRSPPGGAHGSLKTSAMRSNTRYYTGTQSRIRR    1150
MWNDTVRKQTESSFMAGDINSTPTLNRGTMGNHLLTNPVLQPRGGTSPYN    1200
TLIAESVGFNPSSPPVFNSPGSYREPKHPLGGREACGMDTLPLNGNFNNS    1250
YSLRSGDFPPGDGGPEPPRGRNLADAAAFEKMIISELVHNNLRGASGGAK    1300
GPPPEPPVPPVPGVSEDEAGGPGGADRAEIELLYKALEEPLLLPRAQSVL    1350
YQSDLDESESCTAEDGATSRPLSSPPGRDSLYASGANLRDSPSYPDSSPE    1400
GPNEALPPPPPAPPGPPEIYYTSRPPALVARNPLQGYYQVRRPSHEGYLA    1450
APSLEGPGPDGDGQMQLVTSL                                1471
```

FIG. 2B-1

```
gaattcggca cgagccctgg tgatgcgggg caaggccccc cccacagtcc gctgagatca ccgtgccgc cctgcctt cgccatggcc
cgcttggctg cagcactctg gagtctctgt gtgacgactg tcctcgtcac ctctgctacc caaggctga gccgggctgg actcccattt
ggattgatgc gcgggagct agcatgcgaa ggctaccca ttgagctgcg gtgcccggc agtgacgtca tcatggtgga gaatgcaaac
tatgggcgca cagatgacaa gatctgcgat gccgaccctt ttcagatgga gaacgtgcag tgctacctgc ctgacgcctt caaaatcatg
tcacagagat gtaataaccg aacccagtgt gtggtggtgg ccggctctga cgccttttct gaccccctgc ctggaaccta caagtacctg
gaggtgcagt acgactgtgt cccttacaaa gtgagcaga aagtcttcgt gtgccaggg acactgcaga agtgctgaa gccacctcc
acacatgaat cggagcacca gtctggcgca tggtgcaagg accactgca ggcaggtgac cgtatctacg ttatgccctg gatccctac
cgcacggaca cactgaccga gtatgcttcc tgggaggact atgtggctgc acgcacacc accacgtaca gactgccaa ccgtgtagat
ggcactggct ttgtggtata tgatggtgcc gtcttctata acaaggaacg tactcgcaac attgtcaaat atgacctgcg gacccgcatc
agagagcgga aaacagtcat aaacacagcc aacctcacc ttatcgctgg ggaggcaaaa ccgacattga cctggcagtg
gatgaaacg ggctgtgggt catctatgcc acgaggga acaacgggcg tctgtggtg agcagctca acccctacac actgcgtttc
gagggcaccg ggggaacagg ctatgacaag cgctcagct atgcctt catgtgtcct gtgtcctct atgtgctgcg ctctgttat
gtggatgacg acagtgaggc agcaggcaac cgtgtgact gactacaatc ccgggacaa catgccttaa caccaatgca agccgtcag tctcgcttc
cccaacccct accagtttgt atcttctgtt gactacaatc ccgggacaa ccagctgtat gtgtggaaca ctatttcgt ggtgctac
agcctggagt ttgaccccc agatcccagt gctgcccag ccactcccc cacttcccc acctctcagt accaccacca cagctcggcc tacgccctc
accagcacag cctcacctgc agccaccact gctgcccac ccactccgc gggcgccct caccacgcac ccagtaggtg ccatcaacca gctggacct
gacccgcctc cagccacag cccagcacc agtaccccg ggcctcccc aggcctcccc agctctcaac tactaggtc catgtgtccc ctgaaccc
cgagaggtcc ggcgggtcca gtggccagct accagcagg gtatgctggt agagagacct tgcccaagg gaactcgagg aattgcctcg
ttccagtgcc tcccagctct gggctctgg aatcctcggg gcctgacct agctcggc acttcccct gggtcaacca agtcgcccag
aagatcaaga gtggagagaa tgcagccaac attgctagtg cccagctcca tgtgtggag acagtggaca ggctccatct cgtgtcccca
tcggtgaagc tgatgagca actgctagat atcctgatg gactggact atatcggcca atatccaagc agtgttcg gcagagagca
tacaataaga tgcccaagcg agagagaacc tgcagcat gaacaggtcc atacggccac atccatcaat aaggagtcca gccgtgttct cctcatggac
cttgagtcat ggaaagacat gaatgccacc ctggtgcctt aactcacagg tcatcgcagc atcatgcagc cgtgtctt actcagagcg ctcctgctg
gccgacaatg tcagagaaac tgctcgcttc ttggctgcca agcagaatgt ccattcagct gtccgccaac accatcaagc aggagggtgc cttccagtgt
caggagttgg tgttcccca ggagtatgcc agtgagagct ccattccctct gttgtccac accatcaagc agaacagccg caatggtgtg
gtgaagttg tcttcattct ctacaacaaa ctgggcctc tcttgtccac ggagaatgcc acaggagagc tggcaggtga ggcaggacc
ggtggcctg gaggtgcctc ctggtggtt aactcacagg tcatcgcagc atccatcaat aaggagtcca gccgtgtctt cctcatggac
cctgtcatct ttactgtggc ccacttgtgg ccaagaacc acttcaatgc aaactgctcc ttctggaact actcagagcg ctcctgctg
gcctactggt caacccaggg ctgccgactg gtggagtcca ataagaccca taccacatgt gcctgcgcc aggtcaggaa cttcgccaagt
ctcatggctc accgagagat ctaccaaggc cgtattaatg agctgttgct gtcagtcatc acctgggttg gcattgtcat ctccctggtc
```

FIG. 2B-2

```
tgtctggcta tctgcatctc caccttctgc ttcctgcggg gcctgcagac cgaccgcaac accatccaca agaacctgtg catcaacctc
ttccttgcag agctgctctt cctggttgga atagacaaaa gagggcgtgc ctcagtatga gtcgcctgc cctatctttg gcactacttc
ttcctggccg ccttcctctg gctgtgccta gaggcgtgc acctctacct cctgctggtc agagcgaata ttcacgcacc
aagtactatt acctgggcgg ctactgcttc ccagccctgg tggtaggcat cgcagccgcc attgactacg gaagctacgg cactgagaag
gctgctggc tgagggtgga taactatttc atctggagct tcgtctgca cgtctccttt gttattgtgt tgaacctggt gttcctcatg
gtgaccctgc acaagatgat ccgaagctca tccgtgctca agcctgactc cagccgcctt gacaacatca agtcctgggc gctggtgcc
attgcactgc tcttcctgct gggcctcacc tggctttcg gcctcctctt gcctcctctt gacacatca gagtcagtag cctcttcaca
accttcaacg ccttcaggg ggtcttcatc tttgtctttc actgcgcctt actagaaaaag gtgcacaagg agtacagcaa gtgcctgcgt
cactcctact gctgcattcg ctccccacct gggggggctc acggctccct acggctcctca gccatgcgaa gccatgcgaa ctactacaca
gggaccccaga gccgaatccg gaggatgtgg aatgacaccg catgggaaac tgaggaagca caaccctgt ctcctttatgg caacagcacc
ccaccctga acgaggtac ctgtgggctt caatcctcc tgccccctcc tcttcaactc ctgggggca ctagccata caatacactc
attgcagagt ctgtgggctt gtgcatgga ctactgcgcc cttaatgcaa acttcaacaa ccaggaagc cagctactcc ctaagcaccc cttgggcggc
cggaaagcct gtggcatgga agccacccg aggcgaat ctagcggatg ctgcgcctt tgagaagatg atcatctcag agctgtgtgca tcggggat
ggggtccct agcacccg aggcgaat ctagcggatg ctgcgcctt tgagaagatg atcatctcag agctgtgtgca caacaacctt
cggggggca gtggggggcc caaaggtcct caaagagc ctcctgtgcc accgtgcca ggagtcagtg aggacgaggc tgtggcct
gggggtctg accggctga gattgaactt ctctacaagg ccctggagga gccactgctg ctgccccctc cccagtcgt gctgtaccag
agtgatctgg atgagtcgga gagctgtacg gcagaggatg gggcaccag acagcagccc cggccctc ccggccggga ctccctctat
gccagcgggg ccaacctcg ggactgcgc tcctacccgg tcctcttcgt tcttcttcgt ccaccagaaa aatgaggcc tgccccctcc cccacctgct
cccctgggc cccagaaat ctactacacc ctcgcccgc cggccctggt ggctcggaat ccctacagg gctactacca ggtgcggcgg
ccagccatg aggctacct gcagccccca agccttgagg ggccagggcc cgatggggat gggcaaatgc agttggtcac tagtctctga
gggcctcat ggaccagagg cctggccagg gagggaatcc aggaggggct ctggtgggag cagagactga tggaggcagt ggctggtggg
ccactctctc cagtgccc tctgctgccc ggccccacag tcccctgg gactatgacc tggccccag gtgcccaggt tagtagacag
ggttccacc agccacaagc ccagcctct ttaggggagt gcattgagga gaagccccca ggcctagg agtgaggag aagctggtag
gtgtgaccaa cgtcaggat ccccctccct tgagggaga aagcaagga taaggcttcc ctaggtgtac aggggtggcc actttggagg
tggccgaagc cttgcaggat acaccctatc tgctgctcac tcttcttcgt ccaccagaaa ggagcagtgg gacagatgga cagggtcctt
ccatgctaca gttcctttgt tcttggagag atccctgagag agccaggcc caggggatgg atggggttgt gagggctggt
ggttaatggt ggaactttct ctgaagctcc tttctccctt gctattggtc cctatctccc gagcaagcct acctaaacc cccagagtgc
acccactgac cccctccctt gggtgactc ctgatgaagc acaactcccc gcagggcccc aaccactgc agtggccata tttggccagt
tccagtcct gtgggctggg ctatctgggg ctatctgggg agcagatgtg gggtctgggg ctccctgagg agtgggtcct gggtttggat ctttccctag
gggtccctct taccctttct ttcctctctc attgctgtaa atatttcaac aaaaatggaaa aggaaaaaaa aaagacaaaa a
```

FIG. 4A

```
                                                            TM I
                                           .......G...S*..L..^...*             .+.*......R.*.......         .C..........*....W*..E*..L..*
Calcitonin Receptor (Human)                LYYLAIVGHSLSIFTIVLSLGIFV            PRSLGQQRVTLRKNMPLTYILNSMTIIIHL PVSCKILHFFHQTQMACNYFWMLCEGIYLETL
Calcitonin Receptor C1b (Rat)              SYYLALVGHSNSIAALIASWGIPL            FKNLSCQRVTLEKNMFLTYILNSIIIIIHL PISCKILHFFHQTQMACNYFWMLCKGIYLETL
Calcitonin-like Receptor (Rat)             LPFYLFIIGHGLSISLIISLIIPF            PKSLSCQRITLEKNLFSFVCMSIVTIIEL  PVSCKVSQFIHLYLAMGCNYFWMLCEGIYLETL
Corticoliberin Receptor (Mouse)            ALIVHYLGHCVSVVALVAAPLLPL            LRSIRCLRNVIEWNLITTIFILRNIAWFLLQ KVMCRCITIIFNYFVVTNFFWMFVEGCTLETA
Corticoliberin Receptor 2 (Rat)            ALIDMYLGHCISLVALVAAPLLFL            LRSIRCLRNIIEWNLISAPILRNATWFVVQ KVMCRCVTIIFNYFVVTNFFWNFVEGCTLETA
Corticoliberin Receptor 2 (Human)          AVILMYLGHCISLVALLVAAPVLFL           LRSIRCLRNIIEWNLISAPILRNATWFVVQ VGMCRLVTAAYMFHVTNFFWMFGEGCTLETA
Diuretic Hormone Receptor                  ASLYTLAGYISLSLAVLSLAVFVFL           FEDLRCLRNTIETRLMSTYILSACSWILML QTSCMILVICMNYFYLTNFFMRLVEGLYLTNL
CIRL                                       LSVITMVGIYLSLVCLAICISTFC            LRGLQTDRNTIEKNLCINLFLAELLFLVGI RVACPIPAGLLHYIFLAAFSWLCLEKGVBLLYTL
Leukocyte Antigen CD97                     LTLTRVGLALSLPCLLCLLTFL              VRPIQGSRVTIELRLCICLLFVGSTIFLAGI GLRCRLVAGLLHYCLLAAPCMSLRGLEEYTL
EMR1 Receptor                              LYLISBVGIIISLVCLVLAIATPL            CRSIRMENTYLEHLCVCLLAATHLFLAGI KTGCAIIAGFLEYLFLACFFWLVEAVILFLM
Glycoprotein F4/90                         LYLISHVGTVISLVCLALATAFPL            CRAVQMRNTYMEHLCVCLFLAKILFLGIT QTACAIIAGFLEYLFLACFFWKLVEAVNGLFLM
Gastric Inhibitory Peptide Receptor        LQVMTVGYSLSLATLLLALLILS            FRRLECTRNYIEHNLFSFMLRAAAILSRD LAACRTAQIVTQYCVGANYTWLLVEGVYLKSL
Glucagon Receptor                          YQVMNTVGYSLSLGALLAVLLL              LRKLHCTRNYIHQNLFASFVLKAGSVLVID VAGCRVATVIMQYGIIANYCWLLVEGVYLYTIL
Pituitary Adenylate Cyclase Activating Protein VKALYTVGYSTSLVTLTTAMVILC      FRKLHCTRNYIHLHLFLSFILRALSVFIXD TVECKAVNVFFHYCVSNYFWLFIEGLYLFTL
VIP Receptor 2                             VKAITTLGYSVSLMSLATGSIILC            LRRLHCPRNYIHTQLAFFILFASAVFLED WVGCKLSLVFLQYCIMANFMFLLVEGLYLETL
Somatoliberin Receptor                     VKTGYTIGYGLSLATLVATAILS             PRKLHCTRNYIHLHLFISFILRAAAVFIKD TILCKVSVAVSBPATMFSWLLARAVYLSCL
VIP Receptor                               LKVNTTVGYSSSLAMLLVALSLIC            FRKLHCTRNYIBEGLFLSFNLRAVSIFVKD SVGCKAAAVFFQYCVMANFMFWLLVEGLYLETL
Secretin Receptor                          LVNVTTVGYSVSLASLTVAVLLA             FRRLHCTRNYIHLEGLFSFNLRAVSIFVKD KVGCKLVHFPQYCIMANTAMLVTGLYLETL
Parathyroid Hormone Receptor               LGNHITTVGYSVSLASLTVAVLLA            FRRLHCTRNYIHLEGLFLSFNLRAVSIFVKD YAGCKVAVTFLFLATHYYWILYAGLYLESL
```

```
            TM IV                                     TM V                                      TM VI                            TM VII
.........G.^.P........          .C.........*.............         .*....P*....N....*....         .*....*..*G..*..         .QG*....*.C*......V.......
IVANVTEKQRLHMYYLLGNGIPFLVPFTIHAIT DNCMLSVBTHLLYIIHGPVMAALVVNFFFLLNTV LKAVKATMILVPLLGIQFVVFPM YVEBELINPQGFFVATIYCFCNEEVQTTVKR
IVMAVFTEDQRLHHYYLLGNGIPIVFIHAIT  DMCMLSTBTHLLYIIHGPVKAALVVNFFFLLNTV LKAVLATMVLVPLLGIQFVVFPM YLBESIIBPQGFFVATIYCFCNEEVQTLKRR
IVANVTARKQHLMVYYFLGNGPPLLPACHERLA DMCMTSSDTHLLYYIIHGPICALLVNLFFLLNTV KQAVTATILLVLPLLGFLLPHM YVEHILMRYQGLLVSHYIPCFPMGSVQAILR
IVMYYSTEHLRKMLFLIGHCIPCPIIAMAVG  BQCWFGKEAGDLIXYQGPVKLVLLINFFFVLFNIV RQAVLATLVLLPLLGITTMLPFV YPNSFLQSFQGFFVSVTYCFPNGSVRAALRM
IVMYYSTEHLRKMLFLIGNCIPCPIVANAVG  BCNFGKBPGDLIYYQGPIILVLLIMFFVLFNIV  RQAVLATLVLLPLLGITTMLPFV YPMSFLQSFQGFFVSVTYCFPNGSVRSALRK
IVLFYSTDRLRKMMPICIGWCVPFPIVAMAIG IKCVPGKRPGVYIYQGPMILVLLIMFYIFLNPI RKATALALLVLIPLIGLALMLFLLRIH YTRALMLSTQGFTVALFYCPMFTHVRSAIRK
VVETFABNIKLKVYTIIGNGAPAVFITTIMVIS BHCTVMGEQVDWERKAPLLVGLALAHLFLLRIN KGNALGALALELLGLTRAPGLL YLFTTHNAPQGVFIFVHCALQRIVEKSYK
VVRVPQQGLSTRHLCLIGYGVPLLIVGVSAAI RYCWLDFBQGFLMSFLGFVTFYILCNAVIPFTV RALITALAPAQLFLAFAPQLII YVFTIANCLQAFLYLHCLLAKIKVRYKRKR
VVNYFSSRMTKDLRICAPGFGYGLPMCVVFVASAV BRCNLETBTGFINSPLGPVCVTVINSILLATFL RLLATFAPAQLFHLCSNVLGIP YLPTIHSLQGAFIFLHCLLHRGQVRRKRR
VVNTFSSEMIKMLRLCAPGFGYGLFVLVVIIBASV PRCMLPFYTGFINFLGPVCHITINSVLLAMFL LRLIRSTLTLIPLVPLGVBBVVFAP OFFIFLSSFQGELVSVLYCIFCIMIBVQSEIBR
LVLVGGSEHGEPRYTLLGHGHPBRALPVIPNVIV TQCMEBNBVKALMRIRTPLLMYLLINIFFARIL FRLARSTLTLIPLVPLGVBEVVFAP FTDLFFSSFQGLLVAVLYCFLNRGVQSEIRR
LSYFTSEKKSFFELTLCIGNGSPLLFVIPNVVV VQCMEBNDMQGPMULRIFVLLAILIMFPFPARII PRLARSTLLTLIPLIFIPARII VTELGLGSPQGFVAVLYCFLANGRVQAEIKR
LVERFPBRRYTPYWILIGNGFITVCVSVNAML TGCNDNDSTALAVIKGPVVGSIMVMFVFLFLGIGII LRLARTVLVPLLLIPGINTVFAV LPBLGLGSPQGFVAVLYCFLARQRVTEISR
LASYFSREKPATMWLVLAGNGLPVLCTGTNVGC TACWDLDDSSPXWILRGPIVLSVGVNFGLMLII VRLSRSLLTLIIPLPGISHTIIPNF PLEKLGLGSPQGFVAVLYCFLARQVRTEISR
LAVNLPERCFLAYLLIGHGRGTFTVCVSVWAMAL TGCMDTNSSLMNNIIKGPIILTSILVMFIPLCHI SRLARSLLTLIPLLPGISHTIFINTL VPELVVGSPQGFVALYCFLANGSVQAELERR
LAISPFPSERKYLQAPULGWGSPALFVALMAIT TGCWDINANASVWIRGPVILSILVWFIPFINTL KRLAKSLTLILIPLPGISIVPLFAPFINIV FPELALGSPQGLVVAVLYCFLANGEVQLEVQK
IPMAFFEEKKYLMOFTVFGWGLPAVFVAWNSV TGCWDLSSGNEKNIQVFILASIVLWFILFNIV      RKLLESTLVMRPLFGVHITVMA           KYENLPHSFQGFPVALIYCFCNHGVQAEIMK
``` ns herein.# NUCLEIC ACIDS ENCODING A CALCIUM INDEPENDENT RECEPTOR OF α-LATROTOXIN, CHARACTERIZATION AND USES THEREOF This work was supported by Public Health Service grants R01NS35098 and R01NS34937 from the National Institutes of Health. The government may have certain rights herein.

TECHNICAL FIELD OF THE INVENTION

The present invention relates generally to receptors implicated in neurotransmitter release, and particularly to a novel G-protein-coupled receptor which binds α-latrotoxin (α-LTx) independently of calcium ($Ca^{2+}$) presence and is thus a regulator of neurotransmitter release which mediates the calcium-independent stimulation of neurotransmitter release by α-latrotoxin.

BACKGROUND OF THE INVENTION

α-Latrotoxin, a vertebrate neurotoxin of Black Widow Spider venom, is a strong stimulator of spontaneous neurotransmitter release from the nerve terminal (Clark et al.,1970, *Nature*, 225 703–705). In physiological solutions, α-latrotoxin-evoked neurotransmitter release occurs by synaptic vesicle exocytosis and is accompanied by presynaptic membrane polarization and the influx of calcium ions through the channels induced by the toxin and through presynaptic calcium channels. However, an unusual characteristic of α-latrotoxin's stimulatory action is that it does not require extracellular $Ca^{2+}$, provided $Mg^{2+}$ is present in the extracellular solution and can occur even without a noticeable increase in intracellular $Ca^{2+}$ concentration. Stimulation of neurotransmitter release by α-latrotoxin requires binding to its high-affinity membranae receptors. An immunofluorescence study of the neuromuscular junction indicates that the α-latrotoxin receptors may not be restricted to the areas of synaptic contacts. Two types of receptors, differing in their calcium requirement of α-latrotoxin-binding have been described. The calcium-dependent receptor has been identified as neurexin Iα, a member of a large family of multiply spliced neuron-specific proteins, the neurexins. In contrast, brain glycoprotein of the Mr 120,000 which does not belong to the neurexin family recently has been purified and proposed as a calcium-independent receptor for, and a likely mediator of, the calcium-independent stimulation of neurosecretion by α-latrotoxin (Krasnoperov et al., (1996), *Biochem. Biophys. Res. Commun.*, 227:868–875 and Davletov et al., (1996) *J. Biol Chem.* 271, 23239–23245).

α-Latrotoxin receptors have been identified biochemically, using an iodinated radioactive derivative of the toxin by Tzeng and Siekevitz, *J. Neurochem.* (1979) 33, 263–274; Meldolesi, *J. Neurochem.* (1982) 38, 1559–1569; Scheer and Meldolesi, *EMBO J.* (1985) 4, 323–327. These receptors were of low abundance (about 300 fmol/mg of membrane protein), and their affinity to α-latrotoxin was high (Kd in the range of $10^{-9}$–$10^{-10}$ M). Previously, the purification of a high-affinity α-latrotoxin-binding protein was identified as neurexin Iα, a member of a large family of multiply spliced neuron-specific proteins, the neurexins was reported in Petrenko, *FEBS Lett.* (1993) 325, 81–85; Petrenko et al., (1990) EMBO J. 9, 2023–2027; and Ushkaryov et al., *Science* (1992) 257, 50–56. The structural features and developmental profile of neurexins suggest that they perform a function in cell adhesion or recognition important in axonogenesis, see, Ushkaryov et al., *Science* (1992) 257, 50–56; and Puschel and Betz, *J. Neurosci.* (1995) 15, 2849–2856. A hypothesis has been formulated that these highly polymorphic cell surface membrane proteins may define the specificity of synaptic connections in the brain Ushkaryov et al., *Science* (1992) 257, 50–56.

α-Latrotoxin-binding properties of purified and recombinant neurexin-Iα are very similar to the binding properties of the membrane-bound α-latrotoxin receptors with one significant exception: neurexin Iα binds α-latrotoxin only in the presence of calcium, whereas the brain membranes bind the toxin even in the presence of EDTA. Therefore, neurexin Iα may be important in calcium-dependent effects of α-latrotoxin, such as degeneration of nerve terminals, but not in the stimulation of neurosecretion in calcium-independent environment. Since purified α-latrotoxin can form cation channels in artificial lipid bilayers, neurexin Iα may facilitate its insertion into the cellular membrane by binding with α-latrotoxin, resulting in calcium fluxes through the formed cation channels. However, in the absence of calcium, this mechanism would not explain robust stimulation of spontaneous neurotransmitter release by this toxin.

In view of the above, a need therefore exists to elucidate the calcium-independent activation of α-latrotoxin, and to thereby further understand its activity, and possibly devise strategies for intervention that may benefit neuronal activity. It is accordingly toward the fulfillment of these needs that the present invention is directed.

SUMMARY OF THE INVENTION

In one aspect, the present invention concerns the identification of a second α-latrotoxin receptor which binds α-latrotoxin both in the presence or absence of calcium and is pharmacologically and structurally distinct from neurexin Iα, an earlier described receptor of α-latrotoxin. This receptor, designated CIRL (calcium-independent receptor of α-latrotoxin) belongs to the secretin receptor subfamily of G-protein coupled receptors, and, together with α-latrotoxin, interacts with syntaxin, a component of the neuronal exocytotic machinery. CIRL, as a neuronal signaling receptor, is thus critically important for the calcium-independent stimulation of neurotransmitter release by α-latrotoxin. A further aspect of the present invention involves the isolation, purification and characterization of the calcium-independent receptor of α-latrotoxin (CIRL).

In its broadest aspect, the present invention extends to a novel neuronal receptor which is a regulator of neurotransmitter release, and thus mediates α-latrotoxin (α-LTx) toxicity both in the presence or absence of calcium.

In a specific example, the calcium-independent receptor of α-latrotoxin (CIRL) has been identified as a G-protein-coupled receptor which contains a subunit of an apparent Mr 120,000, as determined by SDS-PAGE analysis.

In a still further aspect, the present invention extends to methods of utilizing CIRL. This receptor can be expressed and used to screen libraries of agents, or mixtures of natural origin (e.g., brain homogenates, detergent extracts, cell conditioned media or extracts, etc.) for ligands thereof which can then be utilized in various therapeutic methods.

Still further, since this receptor is enriched in the striatum of the mammalian brain, antibodies or nucleic acid probes thereto can be prepared which can then be utilized in diagnostic methods for screening for the presence of various neurological diseases characterized by the changes in receptor expression, or mutations thereto, or the presence of excess receptors. These diseases include, but are not limited to, neurological diseases such as schizophrenia, Alzheimer's disease, epilepsy, stress disorder, Huntington's disease, Parkinson's disease, as well as peripheral neuromuscular diseases such as myasthenia gravis.

In a particular embodiment, the present invention relates to all members of the herein disclosed family of calcium-independent receptors of α-latrotoxin, and to genetically engineered cells which express such receptors.

The present invention also relates to a recombinant DNA molecule or cloned gene, or a degenerate variant thereof, which encodes a calcium-independent receptor of α-latrotoxin (CIRL); preferably a nucleic acid molecule, in particular a recombinant DNA molecule or cloned gene, encoding the calcium-independent receptor of α-latrotoxin (CIRL), having a nucleotide sequence or is complementary to a DNA sequence shown in FIG. 2B (SEQ ID NO:2). In a still further embodiment, the gene constructs of this invention can be utilized in gene therapy in individuals wherein the lack of, or changes in, or modifications to, this receptor causes deficits in neurotransmission.

The human and murine DNA sequences of the calcium-independent receptor of α-latrotoxin (CIRL) of the present invention or portions thereof, may be prepared as probes to screen for ligands, complementary sequences and genomic clones in the same or alternate species. The present invention extends to probes so prepared that may be provided for screening cDNA and genomic libraries for the calcium-independent receptor of α-latrotoxin (CIRL). For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences set forth in FIG. 2B (SEQ ID NO:2, respectively). Correspondingly, the preparation of antisense RNA and ribozymes are included herein.

The present invention also includes calcium-independent receptor of α-latrotoxin (CIRL) proteins having the activities noted herein, and that display the amino acid sequences set forth and described above and selected from SEQ ID NO:1, and subunits thereof.

In a further embodiment of the invention, the full DNA sequence of the recombinant DNA molecule or cloned gene so determined may be operatively linked to an expression control sequence which may be introduced into an appropriate host. The invention accordingly extends to host cells transformed with the cloned gene or recombinant DNA molecule comprising a DNA sequence encoding the present calcium-independent receptor of α-latrotoxin (CIRL)(s), and more particularly, the complete DNA sequence determined from the sequences set forth above and in SEQ ID NO:2.

According to other preferred features of certain preferred embodiments of the present invention, a recombinant expression system is provided to produce biologically active animal or human calcium-independent α-latrotoxin receptor (CIRL). The transgenic animals can also include a "knock-out" animal as a model of the various diseases.

The concept of the calcium-independent receptor of α-latrotoxin (CIRL) contemplates that specific receptors exist for correspondingly specific ligands, such as α-latrotoxin and the like, as described earlier. Accordingly, the exact structure of each calcium-independent receptor of α-latrotoxin (CIRL) will understandably vary so as to achieve this ligand and activity specificity. It is this specificity and the direct involvement of the calcium-independent receptor of α-latrotoxin (CIRL) in the chain of events leading to release of neurotransmittors, that offers the promise of a broad spectrum of diagnostic and therapeutic utilities.

The present invention naturally contemplates several means for preparation of the calcium-independent receptor of α-latrotoxin (CIRL), including as illustrated herein known recombinant techniques, and the invention is accordingly intended to cover such synthetic preparations within its scope. The isolation of the CDNA and amino acid sequences disclosed herein facilitates the reproduction of the calcium-independent receptor of α-latrotoxin (CIRL) by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate activities of target mammalian cells by interrupting or potentiating the calcium-independent receptor of α-latrotoxin (CIRL). In one instance, the test drug could be administered to a cellular sample with the ligand that activates the calcium-independent receptor of α-latrotoxin (CIRL), or an extract containing the activated calcium-independent receptor of α-latrotoxin (CIRL), to determine its effect upon the binding activity of the calcium-independent receptor of α-latrotoxin (CIRL) to any chemical sample (including DNA), or to the test drug, by comparison with a control.

The assay system could more importantly be adapted to identify drugs or other entities that are capable of binding to the calcium-independent receptor of α-latrotoxin (CIRL) and/or calcium-independent receptor of α-latrotoxin (CIRL) factors or proteins, either in the cytoplasm or in the nucleus, thereby inhibiting or potentiating calcium-independent receptor of α-latrotoxin (CIRL) activity. Such assay would be useful in the development of drugs that would be specific against particular cellular activity, or that would potentiate such activity, in time or in level of activity. For example, such drugs might be used to modulate and/or reverse the degeneration of nerve terminals, to modulate synaptic transmission, or to treat other pathologies, as for example, in making calcium-independent receptor of α-latrotoxin (CIRL) more resistant to α-latrotoxin.

In yet a further embodiment, the invention contemplates antagonists of the activity of a calcium-independent receptor of α-latrotoxin (CIRL). In particular, an agent or molecule that inhibits calcium-independent receptor of α-latrotoxin (CIRL) is an embodiment of the present invention. In a specific embodiment, the antagonist can be a peptide having the sequence of a portion of an calcium-independent receptor of α-latrotoxin (CIRL) domain.

One of the characteristics of the present calcium-independent receptor of α-latrotoxin (CIRL) is that it is a G-coupled-protein having a subunit of apparent Mr 120,000 by SDS-PAGE Analysis.

The diagnostic utility of the present invention extends to the use of the present calcium-independent receptor of α-latrotoxin (CIRL) in assays to screen for calcium-independent receptor of α-latrotoxin (CIRL).

The present invention likewise extends to the development of antibodies against the calcium-independent receptor of α-latrotoxin (CIRL)(s), including naturally raised and recombinantly prepared antibodies. For example, the antibodies could be used to screen expression libraries to obtain the gene or genes that encode the calcium-independent receptor of α-latrotoxin (CIRL)(s). Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating calcium-independent receptor of α-latrotoxin (CIRL) activity.

In particular, antibodies against specifically phosphorylated factors can be selected and are included within the scope of the present invention for their particular ability in following activated protein. Thus, activity of the calcium-independent receptor of α-latrotoxin (CIRL) or of the specific polypeptides believed to be causally connected thereto may therefore be followed directly by the assay techniques discussed later on, through the use of an appropriately labeled quantity of the calcium-independent receptor of α-latrotoxin (CIRL) or antibodies or analogs thereof.

Thus, the calcium-independent receptor of α-latrotoxin (CIRL), their analogs and/or analogs, and any antagonists or antibodies that may be raised thereto, are capable of use in connection with various diagnostic techniques, including immunoassays, such as a radioimmunoassay, using for example, an antibody to the calcium-independent receptor of α-latrotoxin (CIRL) that has been labeled by either radioactive addition, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

The present invention includes an assay system which may be prepared in the form of a test kit for the quantitative analysis of the extent of the presence of the calcium-independent receptor of α-latrotoxin (CIRL), or to identify drugs or other agents that may mimic or block its activity. The system or test kit may comprise a labeled component prepared by one of the radioactive and/or enzymatic techniques discussed herein, coupling a label to the calcium-independent receptor of α-latrotoxin (CIRL), their agonists and/or antagonists, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the calcium-independent receptor of α-latrotoxin (CIRL)(s), genetically engineered cells which express or secrete CIRL, its (or their) subunits, or active fragments thereof, or upon agents or other drugs determined to possess the same activity. A first therapeutic method is associated with the prevention of the manifestations of conditions causally related to or following from the binding activity of the calcium-independent receptor of α-latrotoxin (CIRL) or its subunits, and comprises administering an agent capable of modulating the production and/or activity of the calcium-independent receptor of α-latrotoxin (CIRL) or subunits thereof, either individually or in mixture with each other in an amount effective to prevent the development of those conditions in the host. For example, drugs or other binding partners to the calcium-independent receptor of α-latrotoxin (CIRL) or proteins may be administered to inhibit or potentiate calcium-independent receptor of α-latrotoxin (CIRL) activity, as in the potentiation of calcium-independent receptor of α-latrotoxin (CIRL) in therapy. Also, the blockade of the action of specific phosphatases in the dephosphorylation of activated (phosphorylated) calcium-independent receptor of α-latrotoxin (CIRL) or proteins presents a method for potentiating the activity of the calcium-independent receptor of α-latrotoxin (CIRL) or protein that would concomitantly potentiate therapies based on calcium-independent receptor of α-latrotoxin (CIRL)/protein activation.

More specifically, the therapeutic method generally referred to herein could include the method for the treatment of various pathologies or other cellular dysfunctions and derangements by the administration of pharmaceutical compositions that may comprise effective inhibitors or enhancers of activation of the calcium-independent receptor of α-latrotoxin (CIRL) or its subunits, or other equally effective drugs developed for instance by a drug screening assay prepared and used in accordance with a further aspect of the present invention. For example, drugs or other binding partners to the calcium-independent receptor of α-latrotoxin (CIRL) or proteins, as represented by SEQ ID NO:1, may be administered to inhibit or potentiate calcium-independent receptor of α-latrotoxin (CIRL) activity as in the potentiation of calcium-independent receptor of α-latrotoxin (CIRL) in therapy.

In particular, the proteins of calcium-independent receptor of α-latrotoxin (CIRL) whose sequences are presented in SEQ ID NO:1 herein, their antibodies, agonists, antagonists, active fragments thereof, or expressing cells thereof, could be prepared in pharmaceutical formulations for administration in instances wherein calcium-independent receptor of α-latrotoxin (CIRL) therapy is appropriate, such as to modulate and/or prevent nerve degeneration, or to modulate neurotransmitter release.

Accordingly, it is a principal object of the present invention to provide a calcium-independent receptor of α-latrotoxin (CIRL) and its subunits in purified form that exhibits certain characteristics and activities associated with calcium-independent receptor of α-latrotoxin (CIRL) activity.

It is a further object of the present invention to provide antibodies to the calcium-independent receptor of α-latrotoxin (CIRL) and its subunits, and methods for their preparation, including recombinant means.

It is a further object of the present invention to provide a method for detecting the presence of the calcium-independent receptor of α-latrotoxin (CIRL) and its subunits in mammals in which invasive, spontaneous, or idiopathic pathological states are suspected to be present.

It is a further object of the present invention to provide a method and associated assay system for screening substances such as drugs, agents and the like, potentially effective in either mimicking the activity or combating the adverse effects of the calcium-independent receptor of α-latrotoxin (CIRL) and/or its subunits in mammals.

It is a still further object of the present invention to provide a method for the treatment of mammals to control the amount or activity of the calcium-independent receptor of α-latrotoxin (CIRL) or subunits thereof, so as to alter the adverse consequences of such presence or activity, or where beneficial, to enhance such activity.

It is a still further object of the present invention to provide a method for the treatment of mammals to control the amount or activity of the calcium-independent receptor of α-latrotoxin (CIRL) or its subunits, so as to treat or avert the adverse consequences of invasive, spontaneous or idiopathic pathological states.

It is a still further object of the present invention to provide pharmaceutical compositions for use in therapeutic methods which comprise or are based upon the calcium-independent receptor of α-latrotoxin (CIRL), its subunits, their binding partner(s), or upon agents or drugs that control the production, or that mimic or antagonize the activities of the calcium-independent receptor of α-latrotoxin.

Other objects and advantages will become apparent to those skilled in the art from a review of the ensuing description which proceeds with reference to the following illustrative drawings.

BRIEF DESCRIPTION OF THE DRAWING FIGURES

FIG. 1 is a graph showing two types of α-latrotoxin receptors in brain membranes as detected by lectin inhibition. The specific binding of iodinated α-latrotoxin to rat brain membranes preincubated with different concentrations of Concanavalin A was analyzed in the presence of $Ca^{2+}$ (2 nM) or its absence (3 mM EDTA). Squares and a solid line denotes the binding activity in the absence of calcium. Open circles and a dotted line describes the difference between the binding activity measured in the presence of calcium and in the absence of calcium.

FIG. 2A is the predicted amino acid sequence of CIRL precursor protein.

FIG. 2B is the predicted sequence of DNA encoding CIRL precursor protein.

Figure 3A:
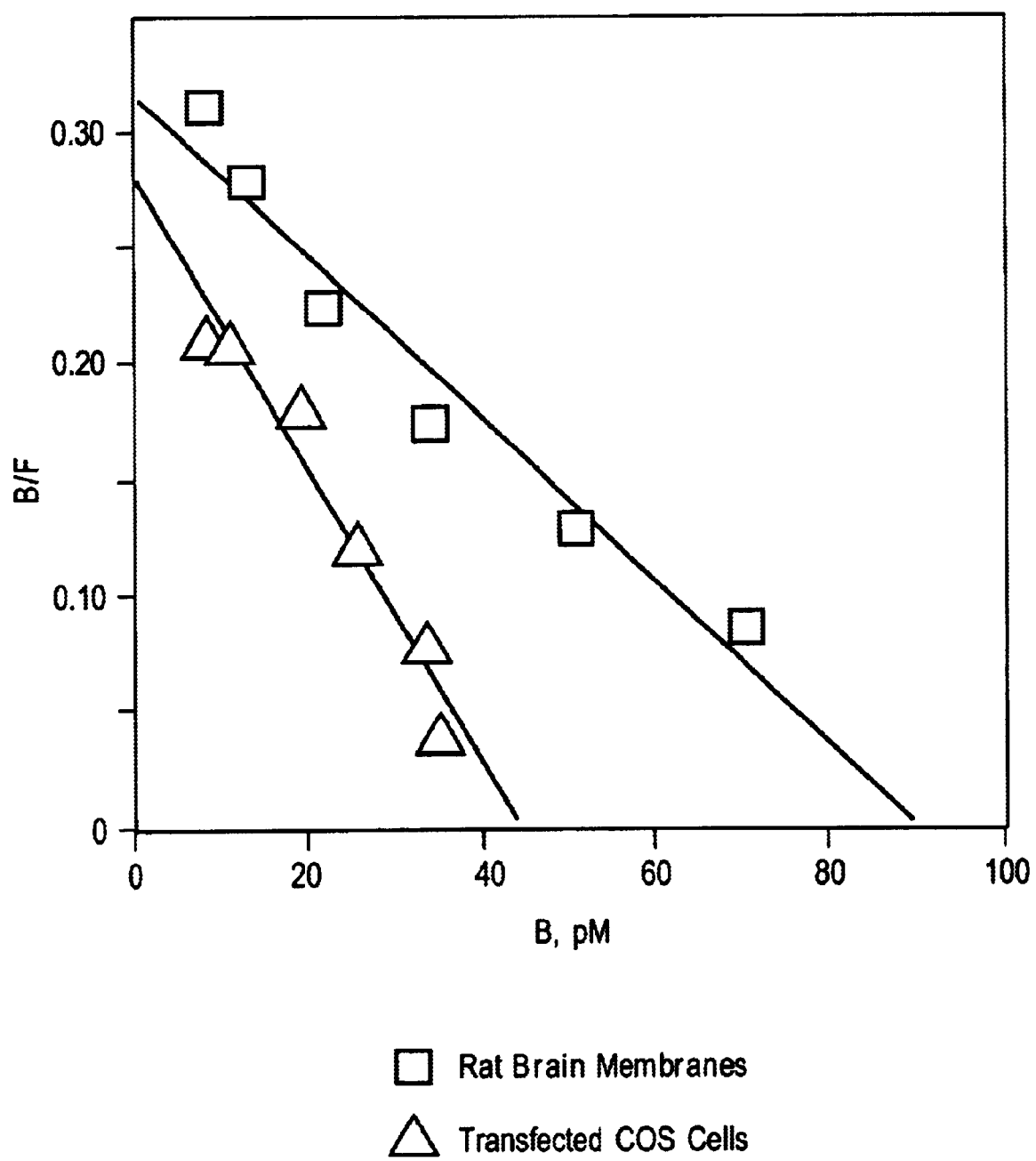

FIG. 3A is a graph showing the expression of functionally active CIRL in COS cells. COS cells were transfected with CIRL expression construct in pcDNA3.1 vector (Invitrogen) by calcium phosphate precipitate method. In two days, the cells were harvested, lysed and crude cell membranes were analyzed for α-latrotoxin binding activity. Approximately 20% of cell material harvested from one 100 mm Petri dish was used for each measurement in the binding assay. In parallel, α-latrotoxin binding activity of rat brain membranes (220 μg protein) was measured under identical conditions. The value of specific binding was calculated by subtraction of the non-specific binding obtained in the presence of 0.1 μM α-latrotoxin from the total binding for each α-latrotoxin concentration. The results of binding assays are presented in a Scatchard plot.

Figure 3B:
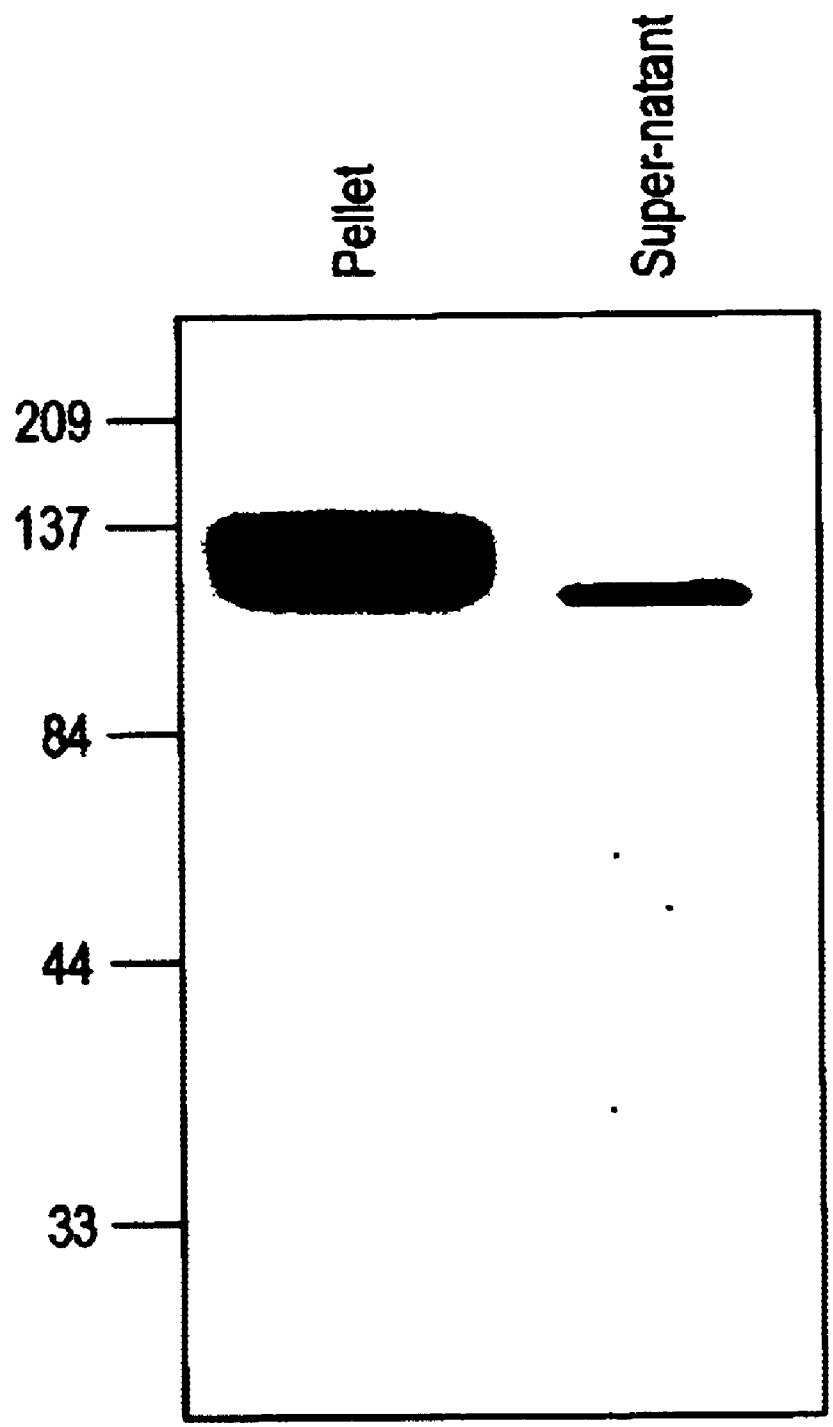

FIG. 3B is a gel showing the binding with anti-Mr 120,000 subunit antibody. COS cells were transfected with an expression plasmid encoding N-terminal 1–850 residues. In two days, the cell media were collected and 1 ml of media was incubated with 10 ml of a latrotoxin-Sepharose for 1 hour at room temperature on a shaker. The mixture was pelleted, the matrix was eluted with SDS sample buffer (pellet) and together with 30 ml of the media (supernatant), analyzed by electrophoresis and Western blotting with anti-Mr 120,000 subunit antibody.

Figure 4B:
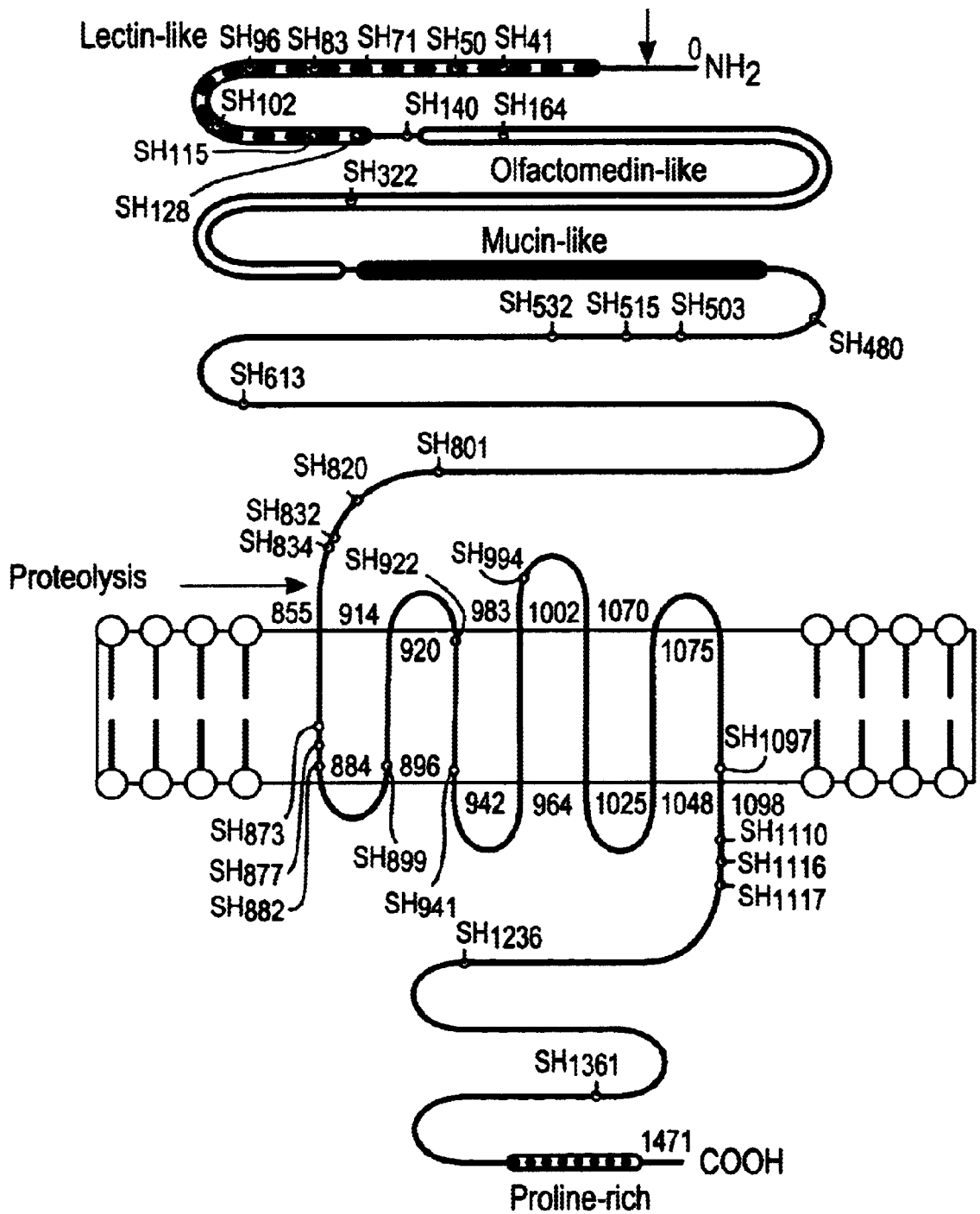

FIGS. 4A–B are diagrams respecting the domain structure of CIRL. FIG. 4A shows homology with a number of the members of the secretin receptor family of proteins.

Accordingly, the following proteins are set forth: calcitonin receptor (human) (SEQ ID NO:13); calcitonin receptor C1b (rat) (SEQ ID NO:14); calcitonin-like receptor (rat) (SEQ ID NO:15); corticoliberin receptor (mouse) (SEQ ID NO:16); corticoliberin receptor 2 (rat) (SEQ. ID NO:17); corticoliberin receptor 2 (human) (SEQ ID NO:18); diuretin hormone receptor (SEQ ID NO:19); CIRL (SEQ ID NO: 20); leukocyte antigen CD97 (SEQ ID NO: 21); EMR1 receptor (SEQ ID NO:22); glycoprotein F4/80 (SEQ ID NO:23); gastric inhibitory peptide receptor (SEQ I) NO:24); glucagon receptor (SEQ ID NO:25); pituitary adenylate cyclase activating protein (SEQ ID NO:26); VIP receptor 2 (SEQ ID NO:27); somatoliberin receptor (SEQ ID NO:28); VIP receptor (SEQ ID NO:29); secretin receptor (SEQ ID NO:30); and parathyroid hormone receptor (SEQ ID NO:31).

Figure 5A:
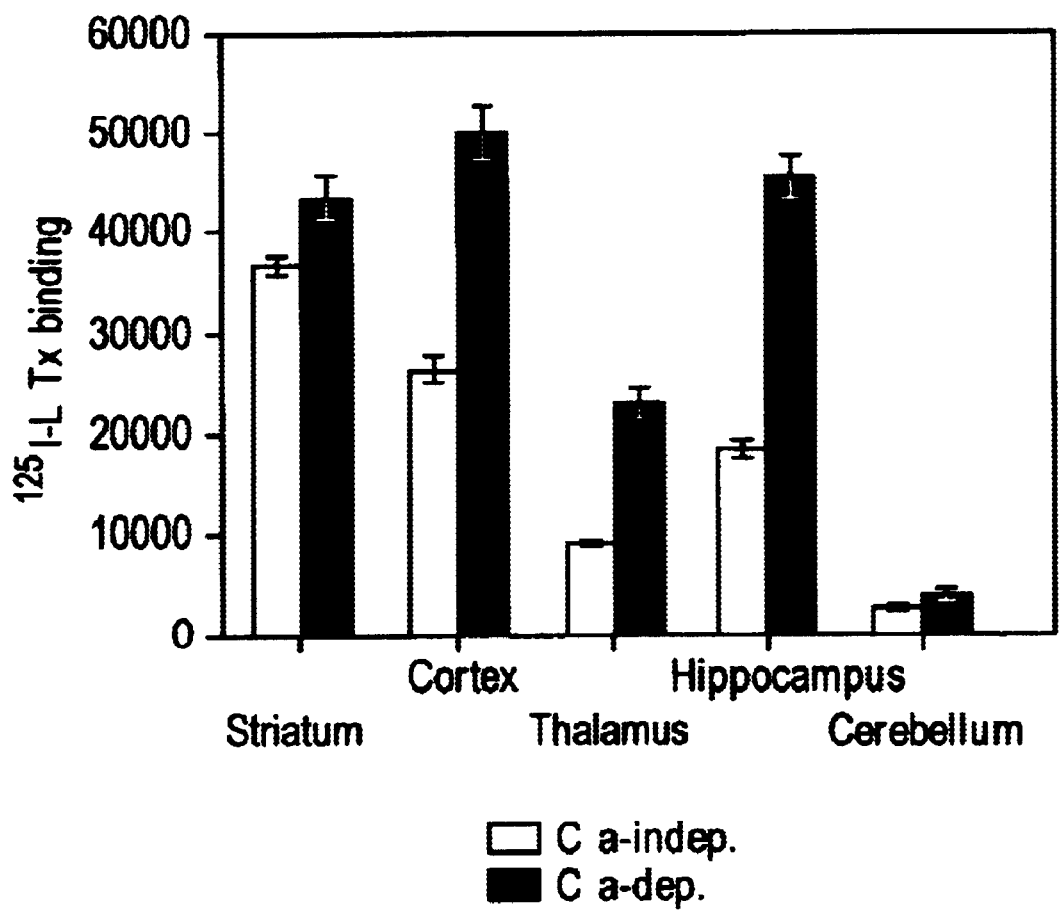
Figure 5B:
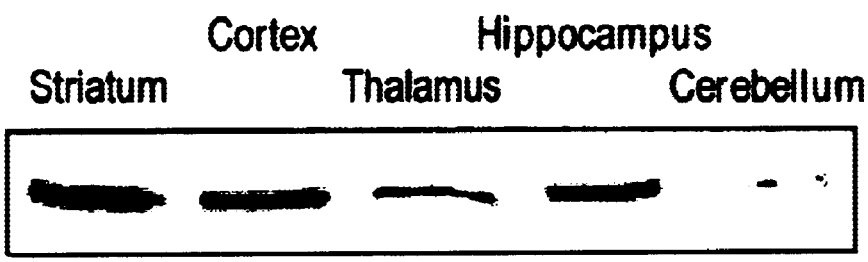

FIG. 5 shows the distribution of CIRL in different brain regions. Rat brains were dissected to separate cortex, striatum, thalamus, hippocampus and cerebellum. The tissues were homogenized in 150 mM NaCl, 50 mM TrisHCl and 2 mM EDTA buffer, pH 7.9 and the crude membrane fractions were obtained by centrifugation. A. The specific binding of 0.5 nM $^{125}$I-α-latrotoxin to the membranes was analyzed in the buffer containing either 2 mM $Ca^{2+}$ or 2 mM EDTA in triplicates. A 100-fold excess of cold α-latrotoxin was added to the control for non-specific binding. Calcium-independent binding activity was calculated as a difference between α-latrotoxin binding measured in the presence of $Ca^{2+}$ and in EDTA-containing buffer. B. The same membrane samples were blotted with the anti-CIRL antibody. When the films of ECL-developed blots with difference exposures were quantitated, all of them showed a larger concentration of CIRL in the striatum than in the cortex by about 40%.

Figure 6:
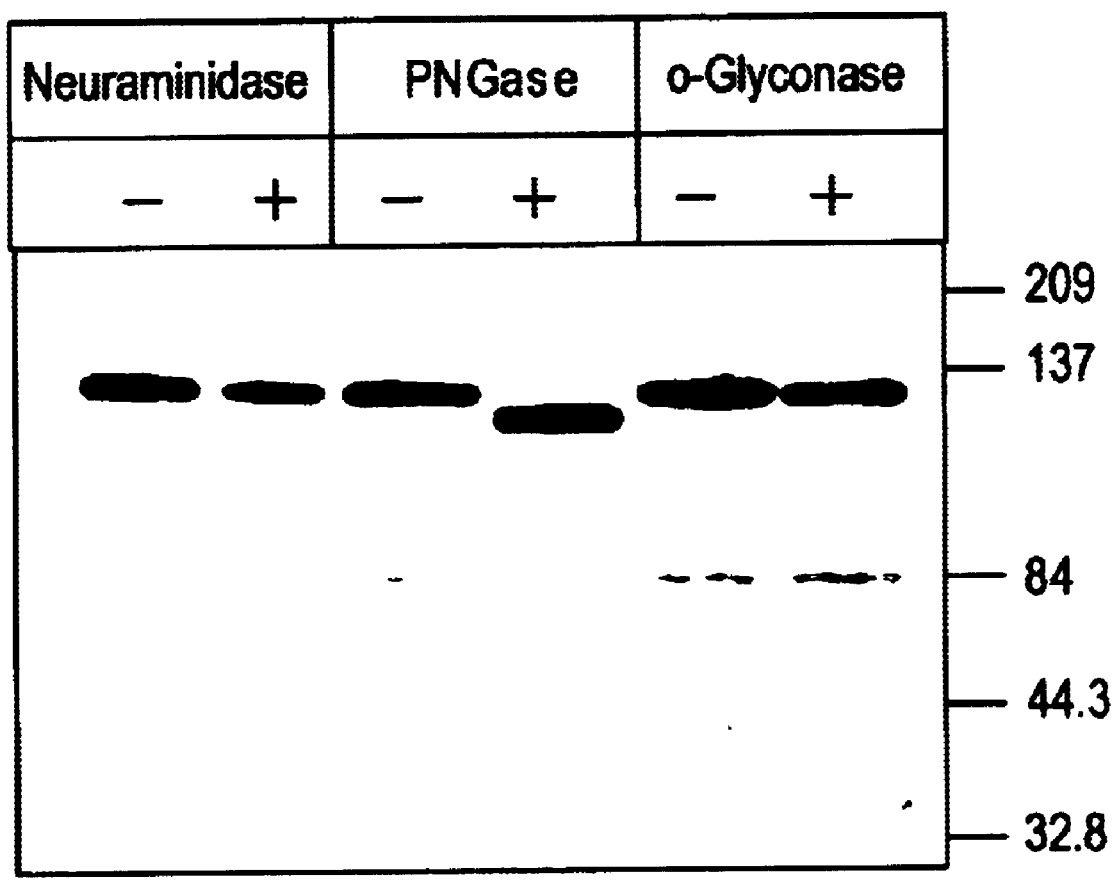

FIG. 6 is a gel showing that CIRL is a glycoprotein. 0.2 mg of affinity purified CIRL were incubated with Neuraminidase, PNGase F and o-Glycanase for 2 hours at 37° C. In control reactions, no enzyme was added. Reaction mixes were resolved on a 10% SDS gel and blotted onto nitrocellulose. The blot was immunostained with anti-CIRL antibody.

Figure 7A:
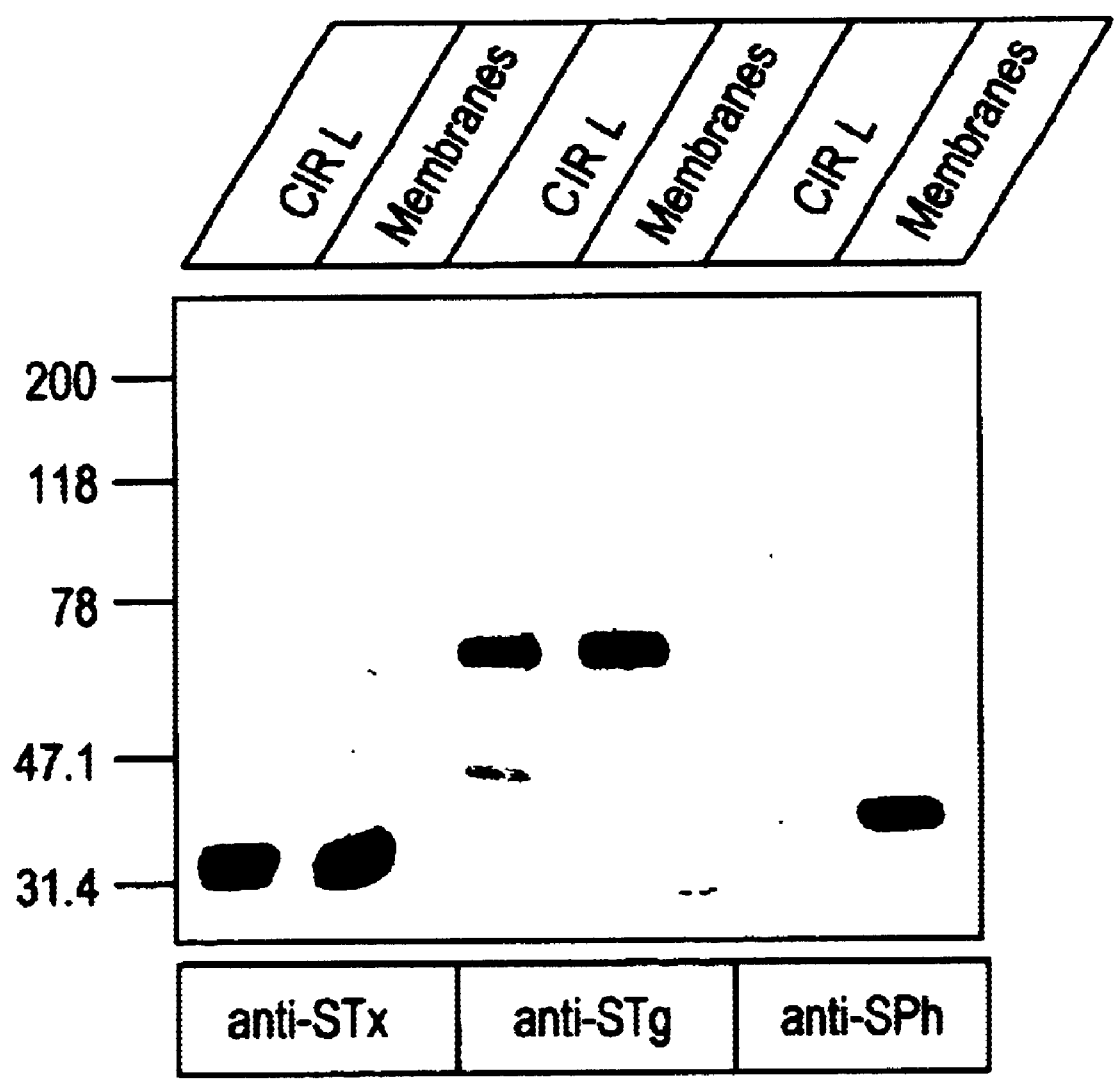
Figure 7B:
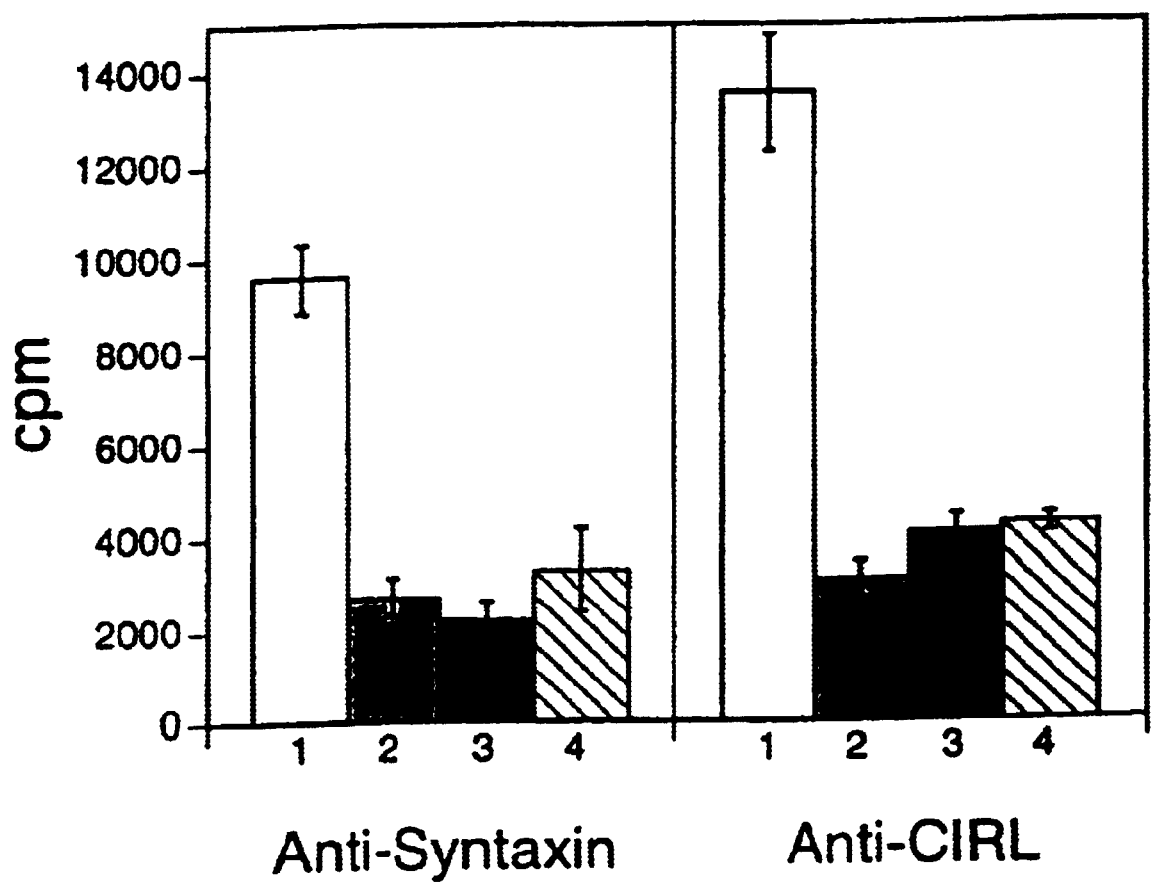

FIGS. 7A and 7B illustrate the interaction of CIRL with syntaxin. FIG. 7A shows the co-purification of syntaxin and synaptotagmin with CIRL on an α-latrotoxin affinity column. The total rat brain membranes in the amount of 35 mg or affinity purified CIRL in the amount of 0.15 mg were loaded on a 9% SDS gel and immunostained with the antibodies against syntaxin (anti-Syx), synaptotagmin (anti-Syt) and synaptophysin (anti-Syph). FIG. 7B shows the immunoprecipitation of α-latrotoxin-binding activity. The complex of $^{125}$I-α-latrotoxin was preformed in the extracts of total brain membranes and immunoprecipitated as described below in the Examples section. Lanes 1—the precipitated binding activity by the corresponding antibody. Lanes 2—no brain membrane extract added. Lane 3—preimmune serum or normal mouse IgGs added to brain extracts. Lane 4—the same as in 3 without brain extracts.

DETAILED DESCRIPTION OF THE INVENTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology:

A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "calcium-independent receptor of α-latrotoxin, "CIRL", and any variants not specifically listed, may be used herein interchangeably, and as used throughout the present application and claims refer to proteinaceous material including single or multiple proteins, and extends to those proteins having the amino acid sequence data described herein and presented in FIG. 2A (SEQ ID NO:1), and active subunits thereof, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "calcium-independent receptor of α-latrotoxin," and "CIRL" are intended to include within their scope proteins specifically recited herein as well as all substantially homologous analogs, allelic variations and active subunits thereof.

The amino acid residues described herein are preferred to be in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

"replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the –10 and –35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending-on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

It should be appreciated that also within the scope of the present invention are DNA sequences encoding the calcium-independent receptor of α-latrotoxin (CIRL) which code for a calcium-independent receptor of α-latrotoxin (CIRL) having the same amino acid sequence as SEQ ID NO:1, but which are degenerate to SEQ ID NO:1. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC or GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in SEQ ID NO:2 such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
 Alanine
 Valine
 Leucine
 Isoleucine
 Proline
 Phenylalanine
 Tryptophan
 Methionine Amino Acids with Uncharged Polar R Groups
  Glycine
  Serine
  Threonine
  Cysteine
  Tyrosine
  Asparagine
  Glutamine
Amino Acids with Charged Polar R Groups (Negatively Charged at pH 6.0)
  Aspartic acid
  Glutamic acid
Basic Amino Acids (Positively Charged at pH 6.0)
  Lysine
  Arginine
  Histidine (at pH 6.0)
Another Grouping May be Those Amino Acids with Phenyl Groups:
  Phenylalanine
  Tryptophan
  Tyrosine
Another Grouping May be According to Molecular Weight (i.e., Size of R Groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, bispecific and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein.

Fab and $F(ab')_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from $F(ab')_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10–20° C. below the predicted or determined $T_m$ with washes of higher stringency, if desired.

In its primary aspect, the present invention concerns the identification of a calcium-independent receptor of α-latrotoxin (CIRL).

In a particular embodiment, the present invention relates to all members of the herein disclosed calcium-independent receptor of α-latrotoxin (CIRL).

As stated above, the present invention also relates to a recombinant DNA molecule or cloned gene which encodes a calcium-independent receptor of α-latrotoxin (CIRL) that possesses an apparent molecular weight of about 120,000 kD, as determined by SDS-PAGE analysis, and an amino acid sequence set forth in FIG. 2A (SEQ ID NO:1). Also, this invention relates to degenerative variants and active fragments of the recombinant DNA molecule.

The possibilities both diagnostic and therapeutic that are raised by the existence of the calcium-independent receptor of α-latrotoxin (CIRL), derive from the fact that this factor appear to be a regulator of neurotransmitter release. As suggested earlier and elaborated further on herein, the present invention contemplates pharmaceutical and/or genetic intervention in the cascade of reactions in which the calcium-independent receptor of α-latrotoxin (CIRL) is implicated.

Thus, in instances where it is desired to reduce or inhibit the activity resulting from a particular stimulus or factor, an appropriate inhibitor of the calcium-independent receptor of α-latrotoxin (CIRL) could be introduced to block the interaction of the calcium-independent receptor of α-latrotoxin (CIRL) with such factors. Correspondingly, instances where insufficient activity is taking place could be remedied by the introduction of additional quantities of the calcium-independent α-latrotoxin receptor or its chemical or pharmaceutical cognates, analogs, fragments and the like.

As discussed earlier, the calcium-independent α-latrotoxin receptor or its binding partners or other ligands or agents exhibiting either mimicry or antagonism to the calcium-independent α-latrotoxin receptor or control over its production, may be prepared in pharmaceutical compositions, with a suitable carrier and at a strength effective for administration by various means to a patient experiencing an adverse medical condition associated with specific α-latrotoxin toxicity for the treatment thereof. A variety of conventional administrative techniques may be utilized, among them parenteral techniques such as subcutaneous, intravenous and intraperitoneal injections, catheterizations and the like. Other administration techniques, including those which utilize cells that have been genetically modified to express CIRL, and/or suitable delivery systems, such as viral vectors, can be utilized to administer the requisite DNA which will then express the CIRL. Average quantities of the calcium-independent receptor of α-latrotoxin (CIRL) or their subunits may vary and in particular should be based upon the recommendations and prescription of a qualified physician or veterinarian.

Also, antibodies including both polyclonal and monoclonal antibodies, and drugs that modulate the production or activity of the calcium-independent receptor of α-latrotoxin (CIRL) and/or their subunits may possess certain diagnostic applications and may for example, be utilized for the purpose of detecting and/or measuring conditions. For example, the calcium-independent receptor of α-latrotoxin (CIRL) or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the calcium-independent receptor of α-latrotoxin (CIRL) of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against calcium-independent receptor of α-latrotoxin (CIRL) peptides can be screened for various properties; i.e., isotype, epitope, affinity, etc. Of particular interest are monoclonal antibodies that neutralize the activity of the calcium-independent receptor of α-latrotoxin (CIRL) or its subunits. Such monoclonals can be readily identified in calcium-independent receptor of α-latrotoxin (CIRL) activity assays. High affinity antibodies are also useful when immunoaffinity purification of native or recombinant calcium-independent receptor of α-latrotoxin (CIRL) is possible.

Preferably, the anti-calcium-independent receptor of α-latrotoxin (CIRL) antibody used in the diagnostic methods of this invention is an affinity purified polyclonal antibody. More preferably, the antibody is a monoclonal antibody (mAb). In addition, it is preferable for the anti-calcium-independent receptor of α-latrotoxin (CIRL) antibody molecules used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to a calcium-independent receptor of α-latrotoxin (CIRL)/protein, such as an anti- calcium-independent receptor of α-latrotoxin (CIRL) antibody, preferably an affinity-purified polyclonal antibody, and more preferably a mAb. In addition, it is preferable for the anti-calcium-independent receptor of α-latrotoxin (CIRL) antibody molecules used herein be in the form of Fab, Fab', F(ab')$_2$ or F(v) portions or whole antibody molecules. As previously discussed, patients capable of benefiting from this method include those suffering from neurological diseases. Methods for inducing anti-calcium-independent receptor of α-latrotoxin (CIRL) antibodies and for determining and optimizing the ability of anti-calcium-independent receptor of α-latrotoxin (CIRL) antibodies to assist in the examination of the target cells are all well-known in the art.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in Antibodies—*A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a calcium-independent receptor of α-latrotoxin (CIRL)-binding portion thereof, or calcium-independent receptor of α-latrotoxin (CIRL), or an origin-specific DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present calcium-independent receptor of α-latrotoxin (CIRL) and their ability to inhibit specified calcium-independent receptor of α-latrotoxin (CIRL) activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium.

The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

General methodology for producing monoclonal anti-calcium-independent receptor of α-latrotoxin (CIRL) antibodies are also well-known in the art. See Niman et al., *Proc. Natl. Acad. Sci. USA*, 80:4949–4953 (1983). Typically, the present calcium-independent receptor of α-latrotoxin (CIRL) or a peptide analog is used either alone or conjugated to an immunogenic carrier, as the immunogen in the before described procedure for producing anti-calcium-independent receptor of α-latrotoxin (CIRL) monoclonal antibodies. The hybridomas are screened for the ability to produce an antibody that immunoreacts with the calcium-independent receptor of α-latrotoxin (CIRL) peptide analog and the present calcium-independent receptor of α-latrotoxin (CIRL).

The present invention further contemplates therapeutic compositions useful in practicing the therapeutic methods of this invention. A subject therapeutic composition includes, in admixture, a pharmaceutically acceptable excipient (carrier) and one or more of a calcium-independent receptor of α-latrotoxin (CIRL), polypeptide analog thereof, fragment thereof, or ligand thereto, as described herein as an active ingredient. In a preferred embodiment, the composition comprises an agent capable of modulating the specific binding of the present calcium-independent receptor of α-latrotoxin (CIRL) within a target cell.

The preparation of therapeutic compositions which contain polypeptides, analogs or active fragments, or ligands as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog, active fragment or ligand can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog-, active fragment- or ligand-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single-stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, especially mammalian cells, such as CHO, R1.1, B-W and L-M cells, African Green Monkey-kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that calcium-independent receptor of α-latrotoxin (CIRL) analogs may be prepared from nucleotide sequences of the protein complex/subunit derived within the scope of the present invention. Analogs, such as fragments, may be produced, for example, by pepsin digestion of calcium-independent receptor of α-latrotoxin (CIRL) material. Other analogs, such as muteins, can be produced by standard site-directed mutagenesis of calcium-independent receptor of α-latrotoxin (CIRL) coding sequences. Analogs exhibiting "calcium-independent receptor of α-latrotoxin (CIRL) activity" such as small molecules, whether functioning as promoters or inhibitors, may be identified by known in vivo and/or in vitro assays.

As mentioned above, a DNA sequence encoding calcium-independent receptor of α-latrotoxin (CIRL) can be prepared synthetically rather than cloned. The DNA sequence can be designed with the appropriate codons for the calcium-independent receptor of α-latrotoxin (CIRL) amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem*., 259:6311 (1984).

Synthetic DNA sequences allow convenient construction of genes which will express calcium-independent receptor of α-latrotoxin (CIRL) analogs or "muteins". Alternatively, DNA encoding muteins can be made by site-directed mutagenesis of native calcium-independent receptor of α-latrotoxin (CIRL) genes or CDNAS, and muteins can be made directly using conventional polypeptide synthesis.

The genes which express CIRL or its analogs or muteins can be utilized in various therapeutic methods. Appropriate vectors for gene delivery are described, for instance, in U.S. Pat. No. 5,173,414 (Lebkowski et al.), U.S. Pat. No. 5,139,941 (Muzyezka et al.), U.S. Pat. No. 4,797,368 (Carter et al. and U.S. Pat. No. 5,252,479 (Srivasta). These, or other similar viral vectors can be utilized for gene therapy so as to effect expression of CIRL.

A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs with unnatural amino acids.

The present invention extends to the preparation of antisense oligonucleotides and ribozymes that may be used to interfere with the expression of the calcium-independent receptor of α-latrotoxin (CIRL) at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into calcium-independent receptor of α-latrotoxin (CIRL)-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for calcium-independent receptor of α-latrotoxin (CIRL) and their ligands.

The present invention also relates to a variety of diagnostic applications, including methods for detecting the presence of stimuli such as the earlier referenced polypeptide ligands, by reference to their ability to elicit the activities which are mediated by the present calcium-independent receptor of α-latrotoxin (CIRL). As mentioned earlier, the calcium-independent receptor of α-latrotoxin (CIRL) can be used to produce antibodies to itself by a variety of known techniques, and such antibodies could then be isolated and utilized as in tests for the presence of particular calcium-independent receptor of α-latrotoxin (CIRL) activity in suspect target cells.

As described in detail above, antibody(ies) to the calcium-independent receptor of α-latrotoxin (CIRL) can be produced and isolated by standard methods including the well-known hybridoma techniques. For convenience, the antibody(ies) to the calcium-independent receptor of α-latrotoxin (CIRL) will be referred to herein as $Ab_1$ and antibody(ies) raised in another species as $Ab_2$.

The presence of calcium-independent receptor of α-latrotoxin (CIRL) in cells can be ascertained by the usual immunological procedures applicable to such determinations. A number of useful procedures are known. Three such procedures which are especially useful utilize either the calcium-independent receptor of α-latrotoxin (CIRL) labeled with a detectable label, antibody $Ab_1$ labeled with a detectable label, or antibody $Ab_2$ labeled with a detectable label. The procedures may be summarized by the following equations wherein the asterisk indicates that the particle is labeled, and "CIRL" stands for the calcium-independent receptor of α-latrotoxin:

A. $CIRL^*+Ab_1=CIRL^*Ab_1$

B. $CIRL+Ab^*=CIRLAb_1^*$

C. $CIRL+Ab_1+Ab_2^*=CIRLAb_1Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, the calcium-independent receptor of α-latrotoxin (CIRL) forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-calcium-independent receptor of α-latrotoxin (CIRL) antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The calcium-independent receptor of α-latrotoxin (CIRL) or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the calcium-independent receptor of α-latrotoxin (CIRL) may be radiolabeled and combined, for example, with antibodies or other inhibitors thereto, after which binding studies would be carried out. Solutions would then be prepared that contain various quantities of labeled and unlabeled uncombined calcium-independent receptor of α-latrotoxin (CIRL), and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of calcium-independent receptor of α-latrotoxin (CIRL) activity in suspected target cells. In accordance with the testing techniques discussed above, one class of such kits will contain at least the labeled calcium-independent receptor of α-latrotoxin (CIRL) or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined calcium-independent receptor of α-latrotoxin (CIRL) activity, comprising:

(a) a predetermined amount of at least one labeled immunochemically reactive component obtained by the direct or indirect attachment of the present calcium-independent receptor of α-latrotoxin (CIRL) factor or a specific binding partner thereto, to a detectable label;

(b) other reagents; and (c) directions for use of said kit.

More specifically, the diagnostic test kit may comprise:

(a) a known amount of the calcium-independent receptor of α-latrotoxin (CIRL) as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol, and comprises:

(a) a labeled component which has been obtained by coupling the calcium-independent receptor of α-latrotoxin (CIRL) to a detectable label;

(b) one or more additional reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an reaction between the calcium-independent receptor of α-latrotoxin (CIRL) and a specific binding partner thereto.

In accordance with the above, an assay system for screening potential drugs effective to modulate the activity of the calcium-independent receptor of α-latrotoxin (CIRL) may be prepared. The calcium-independent receptor of α-latrotoxin (CIRL) may be introduced into a test system, and the prospective drug may also be introduced into the resulting cell culture, and the culture thereafter examined to observe any changes in the calcium-independent receptor of α-latrotoxin (CIRL) activity of the cells, due either to the addition of the prospective drug alone, or due to the effect of added quantities of the known calcium-independent receptor of α-latrotoxin (CIRL).

The following examples are presented in order to more fully illustrate the preferred embodiments of the invention. They should in no way be construed, however, as limiting the broad scope of the invention.

EXAMPLE 1

Two High Affinity α-latrotoxin Receptors in Brain Membranes

Figure 1:
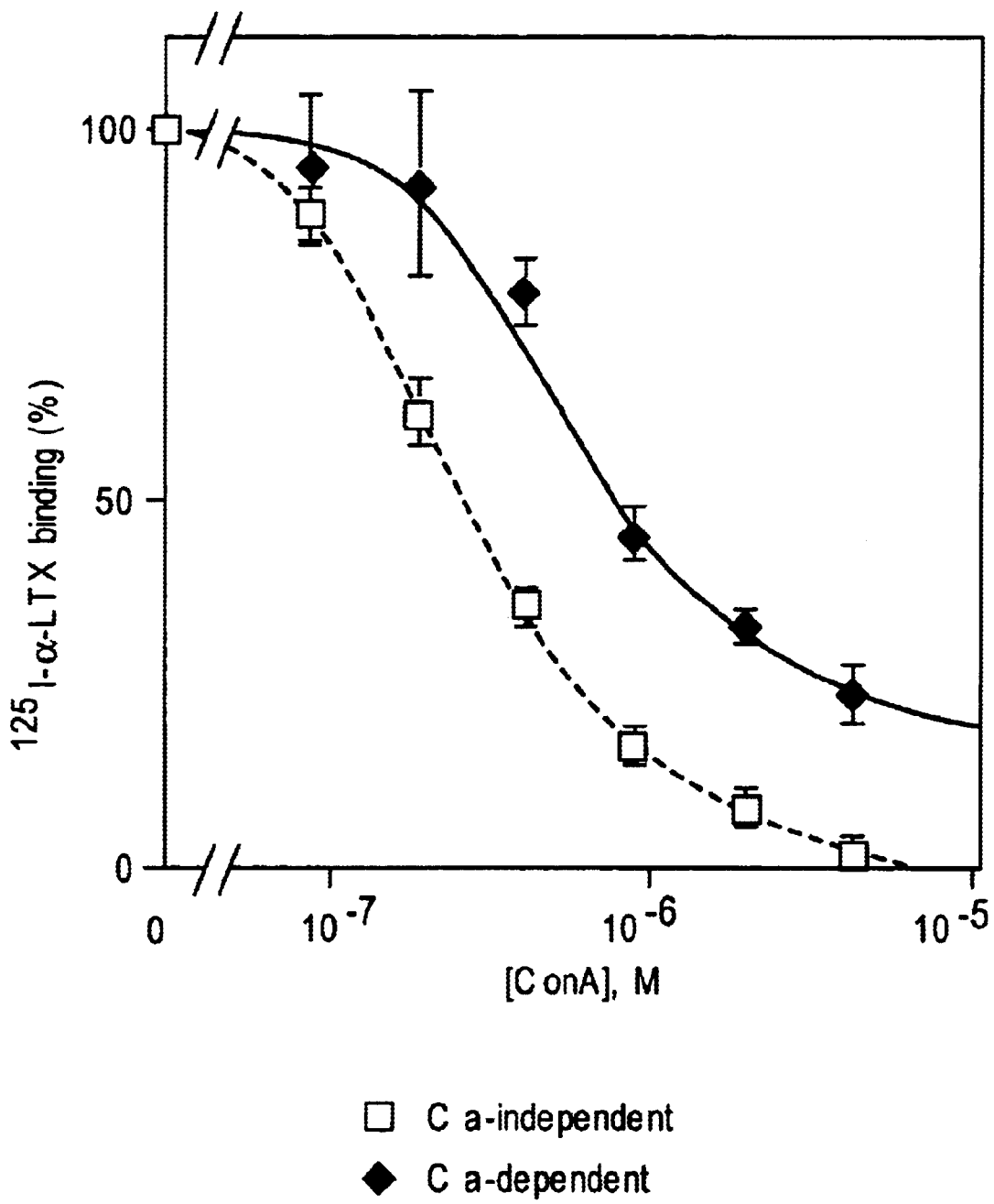

In several independent studies, Scatchard plots of the α-latrotoxin binding activity demonstrated the presence of only one binding site (Rosenthal et al., 1990; Meldolesi, 1982; Tzeng and Siekevitz, 1979a). However, the maximum number of the binding sites was reduced by almost 50% in the presence of calcium chelators (Rosenthal et al., 1990; Tzeng and Siekevitz, 1979a). To analyze whether two receptors of the same affinity exist, or whether there is only one that is partially activated by calcium ions, concanavalin A was used as an antagonist of α-latrotoxin. This lectin inhibits both toxic effects and binding of α-latrotoxin, if it is applied prior to the addition of toxin. The inhibitory effect of Concanavalin A on α-latrotoxin membrane receptors with added calcium ions and with all calcium ions removed by EDTA chelation has been analyzed. The inhibition curves demonstrate a significant difference (approximately 5-fold) in the half-maximum inhibitory effect of Concanavalin A on the calcium-dependent and calcium-independent α-latrotoxin binding sites in brain membranes (see FIG. 1).

Purification and Molecular Cloning of CIRL

Affinity chromatography on immobilized α-latrotoxin columns has been used to purify active α-latrotoxin-binding proteins from brain membrane detergent extracts (Scheer and Meldolesi, 1985; Petrenko et al., 1990). Among them, the Mr 200,000 and 160,000 proteins were identified as isoforms of calcium-dependent high-affinity α-latrotoxin receptor (Petrenko et al., 1990; Petrenko et al., 1993). A protein band of about 120,000 was also detected in the affinity-purified receptor preparations obtained either in calcium-containing or calcium-deficient buffers. This band showed α-latrotoxin immunoreactivity in Western blotting experiments and therefore was initially identified as α-latrotoxin bleeding from the column (Petrenko et al., 1991; O'Connor et al., 1993). However, partial amino acid sequencing of this protein band produced the sequences which were not homologous to α-latrotoxin or any other protein in current databases (Table 1 below).

TABLE 1

PEPTIDE SEQUENCES OF PURIFIED $M_R$ 120,000 PROTEIN

| I | L M E Q L D I L D A | SEQ ID NO: 3 |
|---|---|---|
| II | G I A L F Q Y L P A L G | SEQ ID NO: 4 |
| III | T D G S T E M L S G V D | SEQ ID NO: 5 |
| IV | I Y V M P C I P Y R | SEQ ID NO: 6 |
| V | S L Q L Y V I N A E V I | SEQ ID NO: 7 |
| VI | S G D N A X N I A S E L M V | SEQ ID NO: 8 |
| VIIa | V P V T P G N L Q K | SEQ ID NO: 9 |
| b | Y E G N W E T G Y D K | SEQ ID NO: 10 |
| VIII | V F L M D P V I F T V A H L E A K | SEQ ID NO: 11 |
| IX | X F A V L M A H R E P E | SEQ ID NO: 12 |

Peptide VII gave two sequences which were called separately on the basis of yield ratios.

On the basis of these partial sequences, DNA probes were designed which were used to isolate overlapping clones from rat brain cDNA libraries (see, Experimental procedures, below). One long open reading frame was detected which encodes a novel protein consisting of 1471 amino acid residues (FIG. 2A, SEQ ID NO:1).

The predicted size of the cloned protein was significantly larger than the apparent size of the purified Mr 120,000 protein. The purified receptor proteins were therefore tested to determine whether they contain all of the predicted CIRL sequence by peptide mapping and by analysis with region-specific antibodies. High resolution mass-spectrometry of trypsin-generated peptides revealed the presence of peptides which were attributable to more than 80% of the deduced protein sequence and distributed in a random manner throughout the whole sequence (data not shown). The antibody against the Mr 120,000 protein immunostained only the band of this size in both purified receptor and brain membranes (V. G. Krasnoperov et al., *Biochem. Biophys. Res. Commun.* 227, 868–875 (1996).), while the antibody against the 18 amino acid residues closest to the C-terminus failed to recognize the Mr 120,000 protein and instead reacted with a fuzzy band of about 80,000 Da. However, this C-terminal antibody efficiently immunoprecipitated the Mr 120,000 protein and α-latrotoxin-binding activity from brain detergent extracts. Altogether, these data suggest that CIRL is originally synthesized as a single polypeptide chain which is later proteolytically processed yielding two complexed subunits, the N-terminal glycosylated Mr 120,000 protein containing most of the extracellular domain and the C-terminal Mr 80,000 fragment which includes the transmembrane core and the intracellular domain. This may resemble the proteolytic processing of LDL receptor-related protein, a large transmembrane receptor known to be composed of two subunits derived from the internal cleavage of a precursor (J. Herz, R. C. Kowal, J. L. Goldstein, M. S. Brown, *EMBO J.* 9, 1769–1776 (1990)).

CIRL is a High Affinity Receptor of α-latrotoxin

The identity of CIRL as a high-affinity α-latrotoxin binding protein was directly confirmed by transfections of COS cells, a cell line of non-neuronal origin, with an expression plasmid containing CIRL cDNA (The insert of the longest clone (p87-7) encoding full-length protein was subcloned into pcDNA 3.1, a eucaryotic expression vector (Invitrogen). The resulting plasmid was purified by a midi-prep kit (Invitrogen) and used in transfections of COS-7 cells by the calcium phosphate precipitate method. After two day incubation, the cells were harvested in a cold buffer containing 0.1 M Tris-HCl, 2 mM EDTA, pH 7.9. The cells were lysed by a freeze-thaw procedure, the membranes were pelleted by centrifugation and used for α-latrotoxin-binding assay in a calcium-deficient buffer). The transfected COS cells exhibited high-affinity specific binding of radioactive α-latrotoxin in the absence of calcium (180+/−28 fmol/mg protein in CIRL transfected cells versus 3.9+/−3.3 in mock transfections). Scatchard plot analysis (FIG. 3A) demonstrated that the cells transfected with the CIRL expression construct bound α-latrotoxin with an affinity similar to that of the calcium-independent binding sites in rat brain membranes (calculated Kd=0.16 nM for recombinant receptor, Kd=0.28 nM for brain membranes). Since α-latrotoxin acts extracellularly, the recombinant extracellular domain of CIRL was tested to determine if it by itself would bind α-latrotoxin. COS cells were transfected with the deletion construct encoding the entire extracellular sequence which was expected to get secreted from the transfected cells into the media. The cell conditioned media were further chromatographed on α-latrotoxin-Sepharose and the retained proteins were analyzed by Western blotting with the anti-Mr 120,000 subunit antibody. The immunostaining demonstrated the presence of the band of the expected size (about 120,000) Da) thus confirming interaction of α-latrotoxin with the extracellular portion of CIRL (FIG. 3B).

Structural Features of CIRL

Database searches using BLAST program (NCBI server) revealed significant homology of the CIRL with three recently discovered orphan receptors (the leukocyte activation antigen CD97, EMR1, an EGF module-containing mucin-like hormone receptor and F4/80, a murine macrophage-restricted cell surface glycoprotein, reference 20), members of the secretin receptor family suggesting that CIRL belongs to the G-protein-coupled receptors superfamily. The hydrophobicity plot of CIRL indicates the presence of seven adjacent hydrophobic segments, potential transmembrane helices, which is a hallmark of serpentine G-protein-coupled receptors. The putative transmembrane regions of CIRL are significantly homologous (about 30% identify and 50–60% similarity) to the transmembrane regions of the orphan receptors and other members of the secretin receptor family (21), e.g. secretin receptor, corticoliberin receptor, calcitonin receptor, diuretic hormone receptor, VIP receptor, etc. (FIG. 4A) SEQ ID NOS:13–31. About 10% of amino acid residues in these regions appear to be perfectly conserved among all of the family members. Several other regions of significant homology include the predicted extracellular loops between transmembrane segments I and II, III and IV, IV and V, and a small intracellular region. Two conserved cysteine residues are present in the extracellular loops between segments II and III, and between segments IV and V, that are typical for G-protein-coupled receptors and are thought to form a disulfide bridge on the basis of the structural studies of rhodopsin. Finally, a pair of adjacent cysteines, a potential palmitoylation site, characteristic of G-protein-coupled receptors (Reviewed in H. G. Dohlman, J. Thorner, M. G. Caron, R. J. Lefkowitz, *Ann. Rev. Biochem.* 60, 653–688 (1991).), is found in the cytoplasmic domain close to the transmembrane segments.

On the basis of the hydrophobicity plot and homology searches, the domain model of CIRL which consists of three major regions was proposed, i.e., the large extracellular N-terminal region, the transmembrane region including seven hydrophobic helices and the intracellular C-terminal region, as shown in FIG. 4B. The extracellular domain is proteolytically cleaved somewhere close to the transmembrane helices. This cleavage results in the formation of two subunits that nevertheless does not compromise the integrity of the whole protein. In the very amino terminus of the protein (residues 4–22), CIRL contains a hydrophobic segment, which has the features typical of a secretion signal peptide sequence. This suggests that the amino terminal region of CIRL is located extracellularly which is typical for G-protein-coupled receptors. The most likely site of the signal peptide cleavage is C-terminal to A[21], predicted by sequence homology with known signal peptidase cleavage sites (G. von Heijne, *Nucleic Acids Res.* 14, 4683–4690 (1986).)

Several domains of a large extracellular domain of CIRL, its Mr 120,000 subunit, show significant homology with a galactose-binding lectin from sea urchin eggs (35% identity and 60% similarity, ref. 23), with olfactomedin, a major building block in the extracellular matrix of olfactory neuroepithelium (35% identity and 55% similarity), with olfactomedin-related protein (40% identity and 60% similarity, ref. 24), and with mucin. The homology of CIRL's unusually large extracellular domain to these proteins may suggest its possible function in interacting with glycoproteins of the extracellular matrix and/or membrane of neighboring cells.

Brain-specific Distribution of CIRL

The tissue distribution of CIRL was analyzed by Northern blotting which showed that the Mr 120,000 protein subunit has a brain-specific distribution. Of seven rat tissues analyzed (brain, liver, heart, lung, kidney, spleen, skeletal muscle and duodenum), only brain shows a specifically hybridized band of approximately 6 kbase. The size of this band is close to the size of the longest clone (5391 base) cloned from the rat brain cDNA library which was full-length with respect to the coding sequence.

To compare CIRL concentrations within several regions of the rat brain, Western blotting with the anti-Mr 120,000 antibody was used. Rat brains were dissected to isolate cortex, cerebellum, hippocampus, thalamus and striatum. Crude membranes were prepared from each tissue and analyzed for both α-latrotoxin-binding activity and CIRL immunoreactivity. The highest concentrations of calcium-independent receptors were found in striatum, somewhat lower in cortex and hippocampus, and much less of these receptors were detected in cerebellum (see FIG. 5). Therefore, the distribution of CIRL immunoreactivity was in good agreement with the pattern of calcium-independent α-latrotoxin binding activity, thus supporting CIRL as the calcium-independent brain receptor of α-latrotoxin.

CIRL is a Glycoprotein

The analysis of α-latrotoxin activity and binding to the receptors by Concanavalin A suggested that CIRL might be a glycoprotein. The analysis of tryptic peptides of CIRL by mass spectrometry revealed the presence of mannose-containing glycopeptides. To determine if CIRL is a glycoprotein, it was tested by digestion with three glycosidases, neuraminidase, peptide-N-glycosidase F (PNGase F) and O-glycosidase. Affinity purified CIRL was digested with these enzymes, blotted onto nitrocellulose and immunodecorated with anti-CIRL antibody (FIG. 6). Only PNGase F produced a noticeable change in the apparent size of the protein. This confirms that CIRL is a glycoprotein containing N-attached carbohydrate chain(s). This finding is supported by the presence of seven potential N-glycosylation sites in the predicted protein structure. CIRL may be also O-glycosylated in the mucin-like domain. However, if present, O-glycosylation is not as extensive as N-glycosylation and does not significantly change protein mobility on a gel.

CIRL Interacts with α-latrotoxin and Syntaxin

It had been previously reported that synaptotagmin and syntaxin co-purify with α-latrotoxin receptors in the course of affinity chromatography on α-latrotoxin-Sepharose with calcium-containing buffers when neurexin Iα is the major component of the column eluate (Petrenko et al., 1991; O'Connor et al., 1993). To determine if these proteins were also present in the eluate of an α-latrotoxin affinity column when all stages of purification were performed in EDTA-containing buffers so that neurexin Iα was not retained, the eluate was tested. Syntaxin and synaptotagmin were detected by Western blotting of the eluted receptor preparations but not other nerve terminal proteins such as synaptophysin, SNAP-25, synapsins, rab 3A, synaptobrevin I and II, and Munc 18/nSec1 (FIG. 7A). When the α-latrotoxin affinity column was eluted with a salt gradient, synaptotagmin was found in the beginning of the gradient (0.2–0.3 M salt) (Petrenko et al., 1991) whereas syntaxin co-eluted with CIRL at salt concentrations higher than 0.6 M (Petrenko et al., 1991, and data not shown).

To assure the specificity of complexing of CIRL with α-latrotoxin and syntaxin, anti-syntaxin antibody was tested to determine if it could immunoprecipitate calcium-independent α-latrotoxin binding activity from detergent extracts of total brain membranes. An antibody against CIRL was included in immunoprecipitation reactions as a positive control. As a negative control, pre-immune serum or normal IgGs were used. Additional controls were included to test whether these antibodies were capable of immunoprecipitating the radiolabel by direct interaction with α-latrotoxin where brain membranes were omitted. After incubations and washes, immunomatrices where anti-CIRL and anti-syntaxin antibodies were adsorbed showed significantly higher retention of labeled α-latrotoxin than the control sorbents (FIG. 7B).

Although synaptotagmin was found in the preparations of calcium-independent receptors and it was previously reported that the calcium-ion dependent α-latrotoxin stimulation of neurosecretion but not the calcium-dependent one is impaired in synaptotagmin-deficient PC12 cells (Shoji-Kasai et al., 1994), an anti-synaptotagmin antibody that was tested, failed to immunoprecipitate the complex of CIRL with α-latrotoxin in the absence of calcium (data not shown). Therefore, it remains to be seen whether the interaction of synaptotagmin with CIRL and toxin is specific or may reflect a weaker indirect complexing through syntaxin or possibly some other protein.

It is generally accepted that α-latrotoxin is a specific presynaptic neurotoxin (Okamoto et al., 1971; Frontali et al., 1976). Its physiological action has been most thoroughly studied in vertebrate neuro-muscular junctions. α-Latrotoxin effects on the neuro-muscular junction consists of two phases. Initially, the frequency of spontaneously released acetylcholine quanta increases dramatically (Clark et al., 1970; Ceccarelli and Hurlbut, 1980; Hurlbut et al., 1990). This effect does not critically depend on the presence of calcium if the buffer contains magnesium ions (Misler and Hurlbut, 1979). Later, the stores of neurotransmitter are exhausted (faster without calcium and slower with calcium) and synaptic transmission ceases (Ceccarelli and Hurlbut, 1980). The poisoned nerve terminals degenerate and this process is calcium-dependent (Okamoto et al., 1971; Gorio et al., 1978).

Although α-latrotoxin's primary target is the peripheral nervous system, it also acts as a stimulator of neurotransmitter release in vitro preparations from the central nervous system, such as brain slices, synaptosomes and cell cultures (Tzeng et al., 1978; Meldolesi et al., 1984; Nicholls et al., 1982; Geppert et al., 1994; McMahon et al., 1990). In these systems, α-latrotoxin acts on different types of synapses and there has been no report suggesting that any particular neurotransmitter cannot be released by α-latrotoxin (Rosenthal and Meldolesi, 1989). Therefore, α-latrotoxin is considered as a universal stimulator of neurotransmitter release (Rosenthal and Meldolesi, 1989). In neuronal cell cultures, it also produces a pronounced morphological change—the beads that appear on the membrane of neuronal processes and may be explained by intense exocytosis (Rubin et al., 1978). Moreover, recently reported α-latrotoxin-stimulated secretion of catecholamines from adrenal chromaffin cells (Barnett et al., 1996) and glutamate from astrocytes (Parpura et al., 1995) suggests that α-latrotoxin sensitivity may not be restricted to neurons and α-latrotoxin may be a secretagogue with a wider spectrum of activity.

While not wishing to be bound by any particular mechanism, mechanisms of neurosecretion stimulation by α-latrotoxin can be proposed. Four such hypotheses have been formulated. One is that α-latrotoxin is an ionophore, i.e., it creates cation-permeable channels in the membrane which results in a calcium influx and subsequent stimulation of secretion (Finkelstein et al, 1976, Grasso et al. 1980). Another possibility is that the toxin stimulates cytoskeletal rearrangements causing exocytosis (Tzeng and Siekevitz, 1979a). A third hypotheses is that by receptor stimulation, secondary messenger signaling is triggered (Vicentini and Meldolesi, 1984; Rosenthal et al. 1990). Finally, there is the possibility that α-latrotoxin acts as a membrane fusion protein (Lishko et al., 1990).

Any of the proposed mechanisms implicate the binding of α-latrotoxin to its membrane receptors as a first step. Stimulation of neurotransmitter release by α-latrotoxin have been correlated with its binding to high-affinity membrane receptors (Meldolesi, 1982; Meldolesi et al., 1983). The necessity of binding to specific α-latrotoxin receptors is also supported by existence of Black Widow spider neurotoxins which produce the same physiological effect in different species and do not cross-react or compete for the same binding site (Fritz et al., 1980 and data not shown). α-Latrotoxin receptors were detected in the tissues of the nervous system but not in other tissues. Active α-latrotoxin receptors have been purified by affinity chromatography on α-latrotoxin-Sepharose (Scheer and Meldolesi, 1985; Petrenko et al., 1990). When brain proteins were loaded on the affinity column in the presence of calcium, the material eluted with an EDTA-containing buffer had two major components, the Mr 160,000 and 200,000 proteins. Both of these proteins bind α-latrotoxin with high affinity in the presence of calcium (Petrenko et al., 1990; Petrenko et al., 1993). They have the same protein structure but different carbohydrate modification and belong to the neurexin family of neuron-specific multiply spliced cell surface receptors (Petrenko et al., 1990; Ushkaryov et al., 1992). The extracellular domain of recombinant neurexin Iα binds α-latrotoxin with high affinity in a calcium-dependent manner ($EC_{50}$≈30 mM) (Davletov et al., 1995). Since both native and recombinant neurexin Iα require calcium for α-latrotoxin binding, this protein is probably not involved in the stimulation of spontaneous neurotransmitter release by α-latrotoxin in the absence of calcium. However, they might be important in mediating the nerve terminal degeneration, a calcium-dependent effect of α-latrotoxin.

The data from the literature suggest that the key step in α-latrotoxin-stimulated neurosecretion is the one which is not calcium-dependent. Since brain membranes also contain a smaller quantity of α-latrotoxin high affinity binding sites which are active in EDTA buffers, it is possible that these receptor(s) and not neurexin Iα, are involved in calcium-independent stimulation of neurotransmitter release by α-latrotoxin. These receptors were tested to determine if they are pharmacologically different from neurexin Iα, using Concanavalin A, a well-characterized antagonist of α-latrotoxin. This lectin effectively inhibits both binding (Meldolesi, 1982) and physiological effects (Grasso et al., 1978; Rubin et al., 1978) of α-latrotoxin, when it is prebound to nerve preparations. It was found that the inhibition of calcium-independent receptors by Concanavalin A was significantly stronger than the inhibition of neurexin Iα by the lectin. An analysis of the published data indicates that, in the presence of calcium, Concanavalin A inhibition of α-latrotoxin-stimulated secretion can be achieved at lower concentrations than the complete inhibition of α-latrotoxin binding (Meldolesi, 1982; Grasso et al., 1978; Tzeng and Siekevitz, 1979a; Rubin et al., 1978). This suggests the primary importance of calcium-independent receptors and not neurexins as mediators of α-latrotoxin-stimulated neurosecretion.

We have compared some features of CIRL with the expected features of a putative calcium-independent α-latrotoxin receptor. Firstly, like the calcium-dependent α-latrotoxin receptor, CIRL was detected in brain tissue, but not in a number of other tissues, by Northern and Western blotting. Secondly, the analysis of the distribution of CIRL in brain regions closely correlates with the distribution of the calcium-independent α-latrotoxin-binding activity. Interestingly, unlike calcium-dependent receptors, calcium-independent receptors are more concentrated in the striatum than cortex which coincides with the distribution of CIRL immunoreactivity. CIRL is a glycoprotein that correlates with the known lectin inhibition of both α-latrotoxin activity and receptor binding. Finally, the peptide mixes of the receptor preparations purified by affinity chromatography on α-latrotoxin-Sepharose, did not contain a significant amount of the peptides other than from CIRL according to the mapping by high-resolution mass spectrometry. One cannot be completely rule out the existence of α-latrotoxin-binding homologs or isoforms of CIRL present in lower concentration in the brain or enriched in other secretory tissues. However, all of these data support the idea that CIRL is the major, if not the only, calcium-independent α-latrotoxin receptor.

Previously, the most widely accepted explanation of α-latrotoxin effects was that it acts as an ionophore, creating cation-permeable pores in the membrane which make possible the entry of calcium into the nerve terminal (Grasso et al., *Nature* 283, 774–776 (1980); Nicholls et al., *Proc. Natl. Acad. Sci. USA* 79, 7924–7928 (1982); Wanke et al., *Biochem. Biophys. Res. Commun.* 134, 320–325 (1986); Hurlbut et al., *J. Membr. Biol.* 138, 91–102 (1994).). This view was largely based on the ability of purified α-latrotoxin to form cation channels in artificial lipid bilayers (Finkelstein et al., *Science* 193, 1009–1011 (1976); Robello et al., *J. Membr. Biol.* 95, 55–672 (1987).). The insertion of toxin molecules into the cell membrane, resulting in calcium fluxes through the formed cation channels would be facilitated by binding to any α-latrotoxin receptor, neurexin Iα or CIRL. There is no doubt that calcium fluxes through α-latrotoxin channels are a significant component of the toxin's effects and may be primarily responsible for calcium-dependent nerve terminal degeneration. However, this mechanism would be effectively eliminated in calcium-free media while the robust stimulation of spontaneous neurotransmitter release by α-latrotoxin will still persist. Our data suggest the potential importance of a second mechanism in α-latrotoxin action which involves intracellular signaling through G-proteins. In support of this hypothesis, α-latrotoxin effects were found to be inhibited by agonists of $GABA_\beta$ and $\mu$-opioid receptors, which are G-protein-linked receptors.

GTP is known to be an important molecule involved in exocytosis. However, its role has been largely attributed to its interaction with small GTP-binding proteins of the Rab family. Although heterotrimeric G-proteins have been implicated in regulation of neurosecretion by presynaptic receptors, most of them inhibit neurosecretion. Since CIRL is a target of α-latrotoxin, a strong stimulator of neurosecretion, it is believed that the physiological CIRL may be important in regulating exocytosis and/or endocytosis.

Based on their structural characteristics, endogenous ligands of CIRL can thus be used to modulate and regulate neurotransmitter release and produce α-latrotoxin-like effects on the nerve terminal.

Experimental Procedures

α-Latrotoxin was purified from lyophilized Black Widow Spider venom glands and radioactively labeled with 125I by chloramine T procedure as previously described (Petrenko et al., 1990). The α-latrotoxin binding activity was analyzed by the rapid centrifugation assay (Davletov et al., 1995). SDS-PAGE and Western blotting with ECL detection were performed according to Bio-Rad and Amersham protocols, respectively. Northern blotting was done with a premade multiple tissue blot (Bios Laboratories) according to the manufacturer's protocol with a randomly labeled probe (Boehringer-Mannheim) obtained with a full-length CIRL cDNA fragment.

Protein Purification and Peptide Sequencing

The purification procedure was carried out at 4° C. Approximately 18–25 frozen rat brains (50 g) were homogenized in 1 liter of 20 mM Tris-HCl, pH 7.9, 150 mM NaCl, 2 mM EDTA and 0.1 mM PMSF buffer using a Waring blender for 90 seconds and centrifuged at 10,000 g for 30 minutes. The pellet was resuspended in a glass-teflon homogenizer in 420 ml of the buffer containing 20 mM Tris-HCl, 2 mM EDTA, 0.1 mM PMSF, and 2% Triton X-100. After 30–45 minutes incubation, the insoluble material was pelleted at 100,000 g for 1 hour. A 300–350 ml aliquot of supernatant was supplemented with 5 M NaCl to a final concentration of 100 mM, and loaded onto 10 ml of the α-latrotoxin-Sepharose column at 0.30–0.35 ml/minutes. After washing the column with 600 ml of 20 mM Tris-HCl, 130 mM NaCl, 2 mM EDTA, and 0.1% Triton X-100, the proteins were eluted with 100 ml of 20 mM Tris-HCl, 1.5 M NaCl, 0.1% Triton X-100 and 2 mM EDTA at a flow rate 0.3 ml/minutes. The eluted receptor proteins were electrophoresed on a 10% SDS gel, transferred to immobilon membrane and digested with trypsin. The digest mixture was then fractionated with a size exclusion column, using the buffer containing 50% acetonitrile and 0.2% TFA. Each fraction was further fractionated using a C18 one millimeter micropore HPLC column and a 50 minute linear binary gradient running from 5% buffer B to 90% buffer B (buffer A=2% acetonitrile and 0.09% TFA, buffer B=90% acetonitrile and 0.10% TFA). The flow rate through the column was 50 microliters per minute. The HPLC system used was a Michrome Bioresources Ultrafast Protein Analyzer equipped with a fixed wavelength (1=214 nm) ultraviolet detector. Fractions corresponding to peaks from the ultraviolet detector were analyzed by matrix assisted laser desorption mass spectrometry (Beavis and Chait, 1996). The mass spectra were used to determine how many peptides were contained in the relevant fractions. Fractions with sufficient purity were then loaded onto a polybrene membrane and analyzed using a Perkin-Elmer Procise peptide microsequencer (pulsed-liquid method). The sequences were determined by comparing the results of the automated sequence calling feature of the Procise data system and the results of manual sequence calling. The sequences obtained were then compared with the mass spectra of the appropriate fraction. Once a sequence was verified, it was compared to all known protein and DNA sequences using the BLAST server at NCBI.

Antibodies

Chickens (egg laying hens) were immunized with affinity purified CIRL additionally purified by preparative gel electrophoresis. The antigen solution was mixed with an equal volume of complete Freund's adjuvant and injected subcutaneously in multiple sites. Two boosters followed the initial injection within two week intervals using incomplete Freund's adjuvant. In two weeks after the last boost, the chickens were bled and the serum was used in Western blotting to test the immune response. Eggs were collected daily and used for the purification of chicken egg yolk immunoglobulins (IgY) according to the established procedure (Carroll and Stollar, 1983). The titer and specificity of antibodies was tested in Western blotting with purified CIRL and total brain membranes. The purified antibody stained on protein band of the Mr 120,000 in total brain membranes. However, it did not inhibit α-latrotoxin binding to CIRL indicating that the site of the α-latrotoxin binding was not a strong immunogen probably because it is highly conserved in vertebrates.

Cloning and Sequencing of CIRL

Molecular cloning experiments were performed according to established procedures and protocols (Ushkaryov et al., 1992, Petrenko et al., 1996). The sequence of a 17 residue peptide VFLMDPVIFTVAHLEAK SEQ ID NO: 11, confirmed by mass spectrometry (1930.3 Da), was used to design two degenerate PCR primers. PCR reactions on a rat cDNA random-primed library, resulted in the isolation of a cDNA fragment of the necessary size. This fragment was used as a template in a PCR reaction with 32P-dCTP to generate a probe for the library screening. About 10 overlapping clones were isolated that encoded most of the protein structure. The most 5'-extended clone was randomly labeled and used to screen an oligo-dT-primed rat brain cDNA which resulted in the isolation of a number of clones, one of them was full-length with respect to the coding cDNA. The clones were sequenced by dideoxy automated method using synthetic primers. Several overlapping clones were sequenced completely on both strands.

Cell Transfection Assays

The insert of the longest clone (p87-7) encoding full-length protein was subcloned into pcDNA 3.1, a eucaryotic expression vector (Invitrogen). The resulting plasmid was purified by a midi-prep kit (Invitrogen) and used in transfections of COS cells by the calcium phosphate precipitate method. After a two day incubation, the cells were harvested in a cold buffer containing 0.1 M Tris-HCl, 2 mM EDTA, pH 7.9. The cells were lysed by a freeze-thaw procedure, the membranes were pelleted by centrifugation and used for α-latrotoxin-binding assay in a calcium-deficient buffer. The transfected cells were also analyzed by Western blotting with anti-CIRL antibody.

For the analysis of secondary messenger signaling, COS-7 cells were cultured in Dulbecco's modified Eagle medium containing 10% fetal calf serum under 5% $CO_2$ at 37° C. For transfection, the cells were seeded into 24-well plates at a density of $1 \times 10^5$ cells/well the day before transfection. the media were removed the next day and 0.25 ml of Opti-MEM (Life Technology) containing 2 μl of lipofectamine (Life Technology) and 0.5 μg of plasmid DNA were added to each well. Five hours later the transfection media were replaced with the culture media. The cells were further labeled with 10 μCi/ml of myo-[2-$^3$H]inositol on the following day and the levels of inositol phosphates were determined one day later as previously described with slight modification. The modification was that phosphate buffered saline (no $Ca^{2+}$ and $Mg^{2+}$) was used during the ligand stimulation. All the cDNAs used in these studied were constructed in the expression vectors driven by the CMV promoters.

Immunoprecipitation Reactions

About 3 g of rat brain was homogenized in 30 ml of 20 mM Tris HCl, 150 mM NaCl, 2 mM EDTA, 0.1 mM PMSF, pH 7.9 and centrifuged at 50,000 g for 20 minutes. The pellet was resuspended in 30 ml of 20 mM Tris HCl, 2 mM EDTA, 0.1 mM PMSF, and 2% Triton X-100. After 40 minutes incubation at 4° C. the mixture was centrifuged at 100,000×g for 1 hour. $^{125}$-I-α-Latrotoxin was added to 1.4 ml portions of supernatant, followed by the addition of antibody after 30 minutes. The mixtures were incubated for 2 hours and further absorbed on Protein A Sepharose over night with gentle rotation. The immunoprecipitation reactions were pelleted, the matrices were washed and counted in the gamma-counter.

The following is a list of documents related to the above disclosure and particularly to the experimental procedures and discussions. The documents should be considered as incorporated by reference in their entirety.

Barnett et al. (1996). Single Cell Measurements of Quantal Secretion Induced by α-Latrotoxin from Rat Adrenal Chromaffin Cells: Dependence on Extracellular $Ca^{2+}$. Eur. J. Physiology-Pfluegers Archiv. (in press).

Beavis et al. (1996) in Methods in Enzymology, eds. B. L. Karger and W. S. Hancock, 270A, 519–551.

Carroll et al. (1983). Antibodies to calf thymus RNA polymerase II from egg yolks of immunized hens. J. Biol. Chem. 258, 24–26.

Ceccarelli et al. (1979). Freeze-fracture studies of frog neuromuscular junctions during intense release of neurotransmitter. I. Effects of black widow spider venom and $Ca^{2+}$-free solutions on the structure of the active zone. J. Cell Biol. 81, 163–177.

Ceccarelli et al. (1980). Ca2+-dependent recycling of synaptic vesicles at the frog neuromuscular junction. J. Cell Biol. 87, 297–303.

Clark et al. (1970). Effects of black widow spider venom on the frog neuromuscular junction. Effects on the fine structure of the frog neuromuscular junction. Nature 225, 703–705.

Davletov, et al., (1995). High affinity binding of alpha-latrotoxin to recombinant neurexin Ia. J. Biol. Chem. 270, 23903–23905.

Davletov et al., (1996) J. Biol Chem. 271, 23239–23245.

Dohlman et al. (1991). Model systems for the study of seven-transmembrane-segment receptors. Ann. Rev. Biochem. 60, 653–688.

Finkelstein et al. (1976). Black widow spider venom: effect of purified toxin on lipid bilayer membranes. Science 193, 1009–1011.

Fritz et al. (1980). Different components of black widow spider venom mediate transmitter release at vertebrate and lobster neuromuscular junctions. Nature 283, 486–487.

Frontali et al. (1976). Purification from black widow spider venom of a protein factor causing the depletion of synaptic vesicles at neuromuscular junctions. J. Cell Biol. 68, 462–479.

Geppert et al. (1994). Synaptotagmin I: a major Ca2+ sensor for transmitter release at a central synapse. Cell 79, 717–727.

Gorio et al. (1978). Double mode of action of black widow spider venom on frog neuromuscular junction. J. Neurocytology 7, 193–202.

Grasso et al. (1978). Concanavalin A blocks black widow spider toxin stimulation of transmitter release from synaptosomes. FEBS Lett. 85, 241–244.

Grasso et al. (1980). Black widow spider toxin-induced calcium fluxes and transmitter release in a neurosecretory cell line. Nature 283, 774–776.

Grasso et al. (1993). The secretion of amino acid transmitters from cerebellar primary cultures probed by α-latrotoxin. Neuroscience. 54, 595–604.

Hurlbut et al. (1990). Correlation between quantal secretion and vesicle loss at the frog neuromuscular junction. J. Physiol.—London 425, 501–526.

Hurlbut et al. (1994). Alpha-latrotoxin channels in neuroblastoma cells. J. Membr. Biol. 138, 91–102.

Krasnoperov et al., (1996), Biochem. Biophys. Res. Commun., 227:868–875.

Li et al. (1995). Ca2+-dependent and -independent activities of neural and non neural synaptotagmins. Nature 375, 594–599.

Linial et al. (1995). α-latrotoxin is a potent inducer of neurotransmitter release in Torpedo electric organ-functional and morphological characterization. Eur. J. Neurosci. 7, 42–52.

Lishko et al. (1990). Fusion of negatively charged phospholipid vesicles by alpha-latrotoxin. FEBS Lett. 266, 99–101.

Malgaroli et al. (1989). Distribution of alpha latrotoxin receptor in the rat brain by quantitative autoradiography: comparison with the nerve terminal protein, synapsin I. Neuroscience 32, 393–404.

McMahon et al. (1990). Alpha-latrotoxin releases both vesicular and cytoplasmic glutamate from isolated nerve terminals. J. Neurochem. 55, 2039–2047.

Meldolesi, J. (1982). Studies on alpha-latrotoxin receptors in rat brain synaptosomes: correlation between toxin binding and stimulation of transmitter release. J. Neurochem. 38, 1559–1569.

Meldolesi et al. (1983). The effect of alpha-latrotoxin on the neurosecretory PC12 cell line: studies on toxin binding and stimulation of transmitter release. Neuroscience 10, 997–1009.

Meldolesi et al. (1984). Free cytoplasmic Ca2+ and neurotransmitter release: studies on PC12 cells and synaptosomes exposed to alpha-latrotoxin. Proc. Natl. Acad. Sci. USA 81, 620–624.

Misler et al. (1979). Action of black widow spider venom on quantized release of acetylcholine at the frog neuromuscular junction: dependence upon external Mg2+. Proc. Natl. Acad. Sci. USA 76, 991–995.

Nicholls et al. (1982). alpha-latrotoxin of black widow spider venom depolarizes the plasma membrane, induces massive calcium influx, and stimulates transmitter release in guinea pig brain synaptosomes. Proc. Natl. Acad. Sci. USA 79, 7924–7928.

O'Connor et al. (1993). On the structure of the 'synaptosecretosome'. Evidence for a neurexin/synaptotagmin/syntaxin/Ca2+ channel complex. FEBS Lett. 326, 255–260.

Okamoto et al. (1971). Destruction of mammalian motor nerve terminals by black widow spider venom. Science 172, 733–736.

Parpura et al. (1995). α-latrotoxin stimulates glutamate release from cortical astrocytes in cell culture. FEBS Letters. 360, 266–70.

Petrenko et al. (1990). Isolation and properties of the alpha-latrotoxin receptor. EMBO J. 9, 2023–2027.

Petrenko et al. (1991). Binding of synaptotagmin to the alpha-latrotoxin receptor implicates both in synaptic vesicle exocytosis. Nature 353, 65–68.

Petrenko, A. G. (1993). alpha-Latrotoxin receptor. Implications in nerve terminal function. FEBS Lett 325, 81–85#.

Petrenko et al. (1993). Polypeptide composition of the alpha-latrotoxin receptor. High affinity binding protein consists of a family of related high molecular weight polypeptides complexed to a low molecular weight protein. J. Biol. Chem. 268, 1860–1867.

Petrenko et al. (1996). Structure and Evolution of Neurexophilin. *J. Neurosci.* 16, 4360–4369.

Puschel et al. (1995). Neurexins are differentially expressed in the embryonic nervous system of mice. J. Neurosci. 15, 2849–2856.

Robello et al. (1987). Permeation of divalent cations through alpha-latrotoxin channels in lipid bilayers: steady-state current-voltage relationships. J. Membr. Biol 95, 55–62.

Rosenthal et al. (1990). Mode of action of alpha-latrotoxin: role of divalent cations in Ca2(+)-dependent and Ca2(+)-independent effects mediated by the toxin. Mol. Pharmacol. 38, 917–923.

Rosenthal et al. (1989). Alpha-latrotoxin and related toxins. J. Pharmacol. Ther. 42, 115–134.

Rubin et al. (1978). Effect of concanavalin A on black widow spider venom activity at the neuromuscular junction: implications for mechanisms of venom action. Brain Res. 143, 107–124.

Scheer et al. (1985). Purification of the putative alpha-latrotoxin receptor from bovine synaptosomal membranes in an active binding form. EMBO J. 4, 323–327.

Sher et al. (1988). Intracellular calcium homeostasis in a human neuroblastoma cell line: modulation by depolarization, cholinergic receptors, and alpha-latrotoxin. Journal of Neurochemistry 50, 1708–1713.

Sher et al. (1989). Human neuroblastoma cells acquire regulated secretory properties and different sensitivity to Ca2+ and alpha-latrotoxin after exposure to differentiating agents. Journal of Cell Biology 108, 2291–2300.

Shoji-Kasai et al.(1994). Synaptotagmin I is essential for Ca2+-independent release of neurotransmitter induced by alpha-latrotoxin. FEBS Letters 353, 315–318.

Tzeng et al. (1978). Release of neurotransmitters and depletion of synaptic vesicles in cerebral cortex slices by alpha-latrotoxin from black widow spider venom. Proc. Natl. Acad. Sci. USA 75, 4016–4020.

Tzeng et al. (1979a). The binding interaction between alpha-latrotoxin from black widow spider venom and a dog cerebral cortex synaptosomal membrane preparation. J. Neurochem. 33, 263–274.

Tzeng et al. (1979b). Action of alpha-latrotoxin from black widow spider venom on a cerebral cortex preparation: release of neurotransmitters, depletion of synaptic vesicles, and binding to membrane. Adv. in Cytopharmacol3, 117–127.

Ushkaryov et al. (1992). Neurexins: synaptic cell surface proteins related to the alpha-latrotoxin receptor and laminin. Science 257, 50–56.

Valtorta et al. (1984). Specific localization of the alpha-latrotoxin receptor in the nerve terminal plasma membrane. Journal of Cell Biology 99, 124–132.

Vicentini et al. (1984). alpha Latrotoxin of black widow spider venom binds to a specific receptor coupled to phosphoinositide breakdown in PC12 cells. Biochem. Biophys. Res. Commun. 121, 538–544.

Wanke et al. (1986). alpha Latrotoxin of the black widow spider venom opens a small, non-closing cation channel. Biochem. Biophys. Res. Commun. 134, 320–325.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

---

What is claimed is:

1. An isolated DNA molecule which encodes a calcium-independent receptor of α-latrotoxin (CIRL), selected from the soup consisting of:
   (A) a DNA sequence as set forth in FIG. 2B (SEQ ID NO:2); and
   (B) a DNA sequence encoding a protein having the amino acid sequence as set forth in SEQ ID NO:1.

2. A vector comprising the DNA molecule of claim 1, which is operatively linked to an expression control sequence within said vector.

3. The vector of claim 2, wherein said expression control sequence is selected from the group consisting of the early or late promoters of SV40 or adenovirus, the lac system, the trp system, the TAC system, the TRC system, the major operator and promoter regions of phase λ, the control regions of fd coat protein, the promoter for 3-phosphoglycerate kinase, the promoters of acid phosphatase and the promoters of the yeast α-mating factors.

4. A plasmid comprising the isolated nucleic acid of claim 1.

5. An isolated host cell comprising the plasmid of claim 4.

6. An isolated host cell transformed with a vector comprising a DNA sequence, which encodes a calcium-independent receptor of α-latrotoxin (CIRL), selected from the group consisting of:
   (A) the DNA sequence as set forth in FIG. 2B (SEQ ID NO:2); and
   (B) a DNA sequence encoding a protein having the amino acid sequence as set forth on SEQ ID NO 1,
      wherein said vector is operatively linked to an expression control sequence.

7. The isolated host cell of claim 6 wherein the host cell is selected from the group consisting of E. coli, Pseudomonas, Bacillus, Streptomyces, yeast, CHO, R1.1, B-W, L-M, COS, BSC1, BXC40, BMT10, plant cell, insect cell, mammalian cell, and human cell in cell tissue.

8. An isolated nucleic acid, which encodes a calcium-independent receptor of α-latrotoxin (CIRL), wherein the isolated nucleic acid comprises the sequence as set forth in SEQ ID NO:2.

* * * * *

SEQUENCE LISTING

<160> NUMBER OF SEQ ID NOS: 31

<210> SEQ ID NO 1
<211> LENGTH: 1471
<212> TYPE: PRT
<213> ORGANISM: rat

<400> SEQUENCE: 1

Met Ala Arg Leu Ala Ala Ala Leu Trp Ser Leu Cys Val Thr Thr Val
 1               5                   10                  15

-continued

```
Leu Val Thr Ser Ala Thr Gln Gly Leu Ser Arg Ala Gly Leu Pro Phe
             20                  25                  30

Gly Leu Met Arg Arg Glu Leu Ala Cys Glu Gly Tyr Pro Ile Glu Leu
         35                  40                  45

Arg Cys Pro Gly Ser Asp Val Ile Met Val Glu Asn Ala Asn Tyr Gly
     50                  55                  60

Arg Thr Asp Asp Lys Ile Cys Asp Ala Asp Pro Phe Gln Met Glu Asn
65                  70                  75                  80

Val Gln Cys Tyr Leu Pro Asp Ala Phe Lys Ile Met Ser Gln Arg Cys
                 85                  90                  95

Asn Asn Arg Thr Gln Cys Val Val Ala Gly Ser Asp Ala Phe Pro
             100                 105                 110

Asp Pro Cys Pro Gly Thr Tyr Lys Tyr Leu Glu Val Gln Tyr Asp Cys
         115                 120                 125

Val Pro Tyr Lys Val Glu Gln Lys Val Phe Val Cys Pro Gly Thr Leu
     130                 135                 140

Gln Lys Val Leu Glu Pro Thr Ser Thr His Glu Ser Glu His Gln Ser
145                 150                 155                 160

Gly Ala Trp Cys Lys Asp Pro Leu Gln Ala Gly Asp Arg Ile Tyr Val
                 165                 170                 175

Met Pro Trp Ile Pro Tyr Arg Thr Asp Thr Leu Thr Glu Tyr Ala Ser
             180                 185                 190

Trp Glu Asp Tyr Val Ala Ala Arg His Thr Thr Thr Tyr Arg Leu Pro
         195                 200                 205

Asn Arg Val Asp Gly Thr Gly Phe Val Val Tyr Asp Gly Ala Val Phe
     210                 215                 220

Tyr Asn Lys Glu Arg Thr Arg Asn Ile Val Lys Tyr Asp Leu Arg Thr
225                 230                 235                 240

Arg Ile Lys Ser Gly Glu Thr Val Ile Asn Thr Ala Asn Tyr His Asp
                 245                 250                 255

Thr Ser Pro Tyr Arg Trp Gly Gly Lys Thr Asp Ile Asp Leu Ala Val
             260                 265                 270

Asp Glu Asn Gly Leu Trp Val Ile Tyr Ala Thr Glu Gly Asn Asn Gly
         275                 280                 285

Arg Leu Val Val Ser Gln Leu Asn Pro Tyr Thr Leu Arg Phe Glu Gly
     290                 295                 300

Thr Trp Glu Thr Gly Tyr Asp Lys Arg Ser Ala Ser Asn Ala Phe Met
305                 310                 315                 320

Val Cys Gly Val Leu Tyr Val Leu Arg Ser Val Tyr Val Asp Asp Asp
                 325                 330                 335

Ser Glu Ala Ala Gly Asn Arg Val Asp Tyr Ala Phe Asn Thr Asn Ala
             340                 345                 350

Asn Arg Glu Glu Pro Val Ser Leu Ala Phe Pro Asn Pro Tyr Gln Phe
         355                 360                 365

Val Ser Ser Val Asp Tyr Asn Pro Arg Asp Asn Gln Leu Tyr Val Trp
     370                 375                 380

Asn Asn Tyr Phe Val Val Arg Tyr Ser Leu Glu Phe Gly Pro Pro Asp
385                 390                 395                 400

Pro Ser Ala Gly Pro Ala Thr Ser Pro Pro Leu Ser Thr Thr Thr Thr
                 405                 410                 415

Ala Arg Pro Thr Pro Leu Thr Ser Thr Ala Ser Pro Ala Ala Thr Thr
             420                 425                 430
```

-continued

```
Pro Leu Arg Arg Ala Pro Leu Thr Thr His Pro Val Gly Ala Ile Asn
        435                 440                 445

Gln Leu Gly Pro Asp Leu Pro Pro Ala Thr Ala Pro Ala Pro Ser Thr
    450                 455                 460

Arg Arg Pro Pro Ala Pro Asn Leu His Val Ser Pro Glu Leu Phe Cys
465                 470                 475                 480

Glu Pro Arg Glu Val Arg Arg Val Gln Trp Pro Ala Thr Gln Gln Gly
                485                 490                 495

Met Leu Val Glu Arg Pro Cys Pro Lys Gly Thr Arg Gly Ile Ala Ser
            500                 505                 510

Phe Gln Cys Leu Pro Ala Leu Gly Leu Trp Asn Pro Arg Gly Pro Asp
        515                 520                 525

Leu Ser Asn Cys Thr Ser Pro Trp Val Asn Gln Val Ala Gln Lys Ile
    530                 535                 540

Lys Ser Gly Glu Asn Ala Ala Asn Ile Ala Ser Glu Leu Ala Arg His
545                 550                 555                 560

Thr Arg Gly Ser Ile Tyr Ala Gly Asp Val Ser Ser Val Lys Leu
                565                 570                 575

Met Glu Gln Leu Leu Asp Ile Leu Asp Ala Gln Leu Gln Ala Leu Arg
            580                 585                 590

Pro Ile Glu Arg Glu Ser Ala Gly Lys Asn Tyr Asn Lys Met His Lys
        595                 600                 605

Arg Glu Arg Thr Cys Lys Asp Tyr Ile Lys Ala Val Val Glu Thr Val
610                 615                 620

Asp Asn Leu Leu Arg Pro Glu Ala Leu Glu Ser Trp Lys Asp Met Asn
625                 630                 635                 640

Ala Thr Glu Gln Val His Thr Ala Thr Met Leu Leu Asp Val Leu Glu
                645                 650                 655

Glu Gly Ala Phe Leu Leu Ala Asp Asn Val Arg Glu Pro Ala Arg Phe
            660                 665                 670

Leu Ala Ala Lys Gln Asn Val Val Leu Glu Val Thr Val Leu Ser Thr
        675                 680                 685

Glu Gly Gln Val Gln Glu Leu Val Phe Pro Gln Glu Tyr Ala Ser Glu
    690                 695                 700

Ser Ser Ile Gln Leu Ser Ala Asn Thr Ile Lys Gln Asn Ser Arg Asn
705                 710                 715                 720

Gly Val Val Lys Val Val Phe Ile Leu Tyr Asn Asn Leu Gly Leu Phe
                725                 730                 735

Leu Ser Thr Glu Asn Ala Thr Val Lys Leu Ala Gly Glu Ala Gly Thr
            740                 745                 750

Gly Gly Pro Gly Gly Ala Ser Leu Val Val Asn Ser Gln Val Ile Ala
        755                 760                 765

Ala Ser Ile Asn Lys Glu Ser Ser Arg Val Phe Leu Met Asp Pro Val
    770                 775                 780

Ile Phe Thr Val Ala His Leu Glu Ala Lys Asn His Phe Asn Ala Asn
785                 790                 795                 800

Cys Ser Phe Trp Asn Tyr Ser Glu Arg Ser Met Leu Gly Tyr Trp Ser
                805                 810                 815

Thr Gln Gly Cys Arg Leu Val Glu Ser Asn Lys Thr His Thr Thr Cys
            820                 825                 830

Ala Cys Ser His Leu Thr Asn Phe Ala Val Leu Met Ala His Arg Glu
        835                 840                 845

Ile Tyr Gln Gly Arg Ile Asn Glu Leu Leu Leu Ser Val Ile Thr Trp
```

-continued

```
                  850                855                860
Val Gly Ile Val Ile Ser Leu Val Cys Leu Ala Ile Cys Ile Ser Thr
865                870                875                880

Phe Cys Phe Leu Arg Gly Leu Gln Thr Asp Arg Asn Thr Ile His Lys
            885                890                895

Asn Leu Cys Ile Asn Leu Phe Leu Ala Glu Leu Leu Phe Leu Val Gly
            900                905                910

Ile Asp Lys Thr Gln Tyr Glu Val Ala Cys Pro Ile Phe Ala Gly Leu
            915                920                925

Leu His Tyr Phe Phe Leu Ala Ala Phe Ser Trp Leu Cys Leu Glu Gly
            930                935                940

Val His Leu Tyr Leu Leu Val Glu Val Phe Glu Ser Glu Tyr Ser
945                950                955                960

Arg Thr Lys Tyr Tyr Leu Gly Gly Tyr Cys Phe Pro Ala Leu Val
                965                970                975

Val Gly Ile Ala Ala Ala Ile Asp Tyr Arg Ser Tyr Gly Thr Glu Lys
            980                985                990

Ala Cys Trp Leu Arg Val Asp Asn Tyr Phe Ile Trp Ser Phe Ile Gly
            995                1000                1005

Pro Val Ser Phe Val Ile Val Val Asn Leu Val Phe Leu Met Val Thr
        1010                1015                1020

Leu His Lys Met Ile Arg Ser Ser Val Leu Lys Pro Asp Ser Ser
1025                1030                1035                1040

Arg Leu Asp Asn Ile Lys Ser Trp Ala Leu Gly Ala Ile Ala Leu Leu
                1045                1050                1055

Phe Leu Leu Gly Leu Thr Trp Ala Phe Gly Leu Leu Phe Ile Asn Lys
            1060                1065                1070

Glu Ser Val Val Met Ala Tyr Leu Phe Thr Thr Phe Asn Ala Phe Gln
            1075                1080                1085

Gly Val Phe Ile Phe Val Phe His Cys Ala Leu Gln Lys Lys Val His
            1090                1095                1100

Lys Glu Tyr Ser Lys Cys Leu Arg His Ser Tyr Cys Cys Ile Arg Ser
1105                1110                1115                1120

Pro Pro Gly Gly Ala His Gly Ser Leu Lys Thr Ser Ala Met Arg Ser
                1125                1130                1135

Asn Thr Arg Tyr Tyr Thr Gly Thr Gln Ser Arg Ile Arg Arg Met Trp
                1140                1145                1150

Asn Asp Thr Val Arg Lys Gln Thr Glu Ser Ser Phe Met Ala Gly Asp
            1155                1160                1165

Ile Asn Ser Thr Pro Thr Leu Asn Arg Gly Thr Met Gly Asn His Leu
1170                1175                1180

Leu Thr Asn Pro Val Leu Gln Pro Arg Gly Gly Thr Ser Pro Tyr Asn
1185                1190                1195                1200

Thr Leu Ile Ala Glu Ser Val Gly Phe Asn Pro Ser Ser Pro Val
                1205                1210                1215

Phe Asn Ser Pro Gly Ser Tyr Arg Glu Pro Lys His Pro Leu Gly Gly
            1220                1225                1230

Arg Glu Ala Cys Gly Met Asp Thr Leu Pro Leu Asn Gly Asn Phe Asn
            1235                1240                1245

Asn Ser Tyr Ser Leu Arg Ser Gly Asp Phe Pro Pro Gly Asp Gly Gly
            1250                1255                1260

Pro Glu Pro Pro Arg Gly Arg Asn Leu Ala Asp Ala Ala Phe Glu
1265                1270                1275                1280
```

-continued

Lys Met Ile Ile Ser Glu Leu Val His Asn Asn Leu Arg Gly Ala Ser
            1285                1290                1295

Gly Gly Ala Lys Gly Pro Pro Glu Pro Pro Val Pro Pro Val Pro
        1300                1305                1310

Gly Val Ser Glu Asp Glu Ala Gly Gly Pro Gly Gly Ala Asp Arg Ala
        1315                1320                1325

Glu Ile Glu Leu Leu Tyr Lys Ala Leu Glu Glu Pro Leu Leu Leu Pro
        1330                1335                1340

Arg Ala Gln Ser Val Leu Tyr Gln Ser Asp Leu Asp Glu Ser Glu Ser
1345                1350                1355                1360

Cys Thr Ala Glu Asp Gly Ala Thr Ser Arg Pro Leu Ser Ser Pro Pro
            1365                1370                1375

Gly Arg Asp Ser Leu Tyr Ala Ser Gly Ala Asn Leu Arg Asp Ser Pro
            1380                1385                1390

Ser Tyr Pro Asp Ser Ser Pro Glu Gly Pro Asn Glu Ala Leu Pro Pro
            1395                1400                1405

Pro Pro Ala Pro Pro Gly Pro Pro Glu Ile Tyr Tyr Thr Ser Arg
    1410                1415                1420

Pro Pro Ala Leu Val Ala Arg Asn Pro Leu Gln Gly Tyr Tyr Gln Val
1425                1430                1435                1440

Arg Arg Pro Ser His Glu Gly Tyr Leu Ala Ala Pro Ser Leu Glu Gly
                1445                1450                1455

Pro Gly Pro Asp Gly Asp Gly Gln Met Gln Leu Val Thr Ser Leu
        1460                1465                1470

<210> SEQ ID NO 2
<211> LENGTH: 5391
<212> TYPE: DNA
<213> ORGANISM: rat

<400> SEQUENCE: 2
gaattcggca cgagccctgg tgatgcgggg caaggccccc cccacagtcc gctgagatca      60
ccgtgcccgc ccctggcctt cgccatggcc cgcttggctg cagcactctg gagtctctgt     120
gtgacgactg tcctcgtcac ctctgctacc caaggcctga gccgggctgg actcccattt     180
ggattgatgc gccgggagct agcatgcgaa ggctacccca ttgagctgcg gtgcccgggc     240
agtgacgtca tcatggtgga gaatgcaaac tatgggcgca cagatgacaa gatctgcgat     300
gccgaccctt ttcagatgga gaacgtgcag tgctacctgc ctgacgcctt caaaatcatg     360
tcacagagat gtaataaccg aacccagtgt gtggtggtgg ccggctctga cgcctttcct     420
gaccccctgtc ctggaaccta caagtacctg gaggtgcagt acgactgtgt cccttacaaa     480
gtggagcaga aagtcttcgt gtgcccaggg acactgcaga aggtgctgga gcccacctcc     540
acacatgaat cggagcacca gtctggcgca tggtgcaagg acccactgca ggcaggtgac     600
cgtatctacg ttatgccctg gatccccctac cgcacggaca cactgaccga gtatgcttcc     660
tgggaggact atgtggctgc acgccacacc accacgtaca gactgcccaa ccgtgtagat     720
ggcactggct ttgtggtata tgatggtgcc gtcttctata caaggaacg tactcgcaac     780
attgtcaaat atgacctgcg gacccgcatc aagagcggag aaacagtcat aaacacagcc     840
aactaccacg acacctcacc ttatcgctgg ggaggcaaaa ccgacattga cctggcagtg     900
gatgagaacg gctgtgggt catctatgcc accgagggga caacgggcg tctggtggtg     960
agccagctca cccctacac actgcgtttc gagggcacct gggaaacagg ctatgacaag    1020

-continued

```
cgctcagcct ccaatgcctt catggtgtgt ggtgtcctct atgtgctgcg ctctgtttat   1080
gtggatgacg acagtgaggc agcaggcaac cgcgtggact atgcctttaa caccaatgca   1140
aaccgagagg agcccgtcag tctcgccttc cccaaccoct accagtttgt atcttctgtt   1200
gactacaatc cccgggacaa ccagctgtat gtgtggaaca actatttcgt ggtgcgctac   1260
agcctggagt ttggaccccc agatcccagt gctggcccag ccacttcccc acctctcagt   1320
accaccacca cagctcggcc tacgcccctc accagcacag cctcacctgc agccaccact   1380
ccactccgcc gggcgcccct caccacgcac ccagtaggtg ccatcaacca gctgggacct   1440
gacctgcctc cagccacagc cccagcaccc agtacccggc ggcctccagc ccccaatctg   1500
catgtgtccc ctgagctctt ctgtgaaccc cgagaggtcc ggcgggtcca gtggccagct   1560
acccagcagg gtatgctggt agagagacct tgccccaagg gaactcgagg aattgcctcg   1620
ttccagtgcc tcccagctct ggggctctgg aatcctcggg gccctgacct cagcaactgc   1680 acttcccect gggtcaacca gtcgcccag aagatcaaga gtggagagaa tgcagccaac   1740
attgctagtg agctggcccg ccacacgcgg ggctccatct atgctgggga cgtgtcctca   1800
tcggtgaagc tgatggagca actgctagat atcctggatg cccagctcca ggccctacgg   1860
cccattgaac gagagtcagc tggcaagaac tacaataaga tgcacaagcg agagagaacc   1920
tgcaaggact atatcaaggc tgtggtggag acagtggaca acctgcttcg gccagaggca   1980
cttgagtcat ggaaagacat gaatgccacc gaacaggtcc atacggccac catgctccta   2040
gatgtcttag aggagggtgc cttcctgctg ccgacaatg tcagagaacc tgctcgcttc   2100
ttggctgcca agcagaatgt ggtcctggag gtcactgtcc tgagcacaga gggtcaagtg   2160
caggagttgg tgttccccca ggagtatgcc agtgagagct ccattcagct gtccgccaac   2220
accatcaagc agaacagccg caatggtgtg gtgaaggttg tcttcattct ctacaacaac   2280
ctgggcctct tcttgtccac ggagaatgcc acagtgaagc tggcaggtga ggcagggacc   2340
ggtggccctg gaggtgcctc cctggtggtt aactcacagg tcatcgcagc atccatcaat   2400
aaggagtcca gccgtgtctt cctcatggac cctgtcatct ttactgtggc ccacttggag   2460
gccaagaacc acttcaatgc aaactgctcc ttctggaact actcagagcg ctccatgctg   2520
ggctactggt caaccagggg ctgccgactg gtggagtcca ataagaccca taccacatgt   2580
gcctgcagcc acctcaccaa cttcgcagtg ctcatggctc accgagagat ctaccaaggc   2640
cgtattaatg agctgttgct gtcagtcatc acctgggttg gcattgtcat ctccctggtc   2700
tgtctggcta tctgcatctc caccttctgc ttcctgcggg gcctgcagac cgaccgcaac   2760
accatccaca gaacctgtg catcaacctc ttccttgcag agctgctctt cctggttgga   2820
atagacaaaa ctcagtatga ggtcgcctgc cctatctttg cgggcctgct gcactacttc   2880
ttcctggccg ccttctcctg gctgtgccta gagggcgtgc acctctacct cctgctggtc   2940
gaggtgttcg agagcgaata ttcacgcacc aagtactatt acctgggcgg ctactgcttc   3000
ccagccctgg tggtaggcat cgcagccgcc attgactacc gaagctacgg cactgagaag   3060
gcctgctggc tgagggtgga taactatttc atctggagct tcattgggcc cgtctccttt   3120
gttattgtgg tgaacctggt gttcctcatg gtgaccctgc acaagatgat ccgaagctca   3180
tccgtgctca agcctgactc cagccgcctt gacaacatca gtcctgggc gctgggtgcc   3240 attgcactgc tcttcctgct gggcctcacc tgggctttcg gcctcctctt catcaacaag   3300
gagtcagtag taatggctta cctcttcaca accttcaacg ccttccaggg ggtcttcatc   3360
tttgtctttc actgcgcctt acagaaaaag gtgcacaagg agtacagcaa gtgcctgcgt   3420
```

-continued

```
cactcctact gctgcattcg ctccccacct ggggggctc acggctccct taagacctca    3480
gccatgcgaa gtaacacccg ctactacaca gggacccaga gccgaatccg gaggatgtgg    3540
aatgacaccg tgaggaagca gacagagtcg tcctttatgg caggggacat caacagcacc    3600 cccacccctga accgaggtac catggggaac cacctactga ccaaccctgt gctacagccc    3660
cgtgggggca ctagcccata caatacactc attgcagagt ctgtgggctt caatccctcc    3720
tcgcccccag tcttcaactc cccaggaagc tacagggaac taagcaccc cttgggcggc    3780 cgggaagcct gtggcatgga cacactgccc cttaatggca acttcaacaa cagctactcc    3840
ttgcgaagtg gtgatttccc tccggggggat ggggtcctg agccaccccg aggccgaaac    3900
ctagcggatc ctgcggcctt tgagaagatg atcatctcag agctggtgca caacaacctt    3960 cgggggggcca gtggggggcgc caaaggtcct ccaccagagc tcctgtgcc acccgtgcca    4020 ggagtcagtg aggacgaggc tggtgggcct ggggtgctg accgggctga gattgaactt    4080
ctctacaagg ccctggagga gccactgctg ctgccccggg cccagtcggt gctgtaccag    4140
agtgatctgg atgagtcgga gagctgtacg gcagaggatg gggccaccag ccggcccctc    4200
tcctcccctc ccggccggga ctccctctat gccagcgggg ccaacctgcg ggactcgccc    4260
tcctacccgg acagcagccc cgaagggcct aatgaggccc tgcccctcc ccacctgct    4320 cccctgggc ccccagaaat ctactacacc tctcgcccgc cggccctggt ggctcggaat    4380
cccctacagg gctactacca ggtgcggcgg cccagccatg agggctacct ggcagccccc    4440
agccttgagg ggccagggcc cgatggggat gggcaaatgc agttggtcac tagtctctga    4500
ggggcctcat ggaccagagg cctggccagg gagggaatcc aggagggct ctggtgggag    4560 cagagactga tggaggcagt ggctggtggg ccactctctc caggtgcccc tctgcctgtg    4620
ggccccacag tccccttggg gactatgacc tgggccccag gtgccagggt tagtagacag    4680
ggtttccacc agccacaagc cccagcctct ttaggggagt gcattgagga aagcccca    4740 gggccctagg agtgagggag aagctggtag gtgtgaccaa cgtccaaagc tccctcccctt    4800 tggagggaga aagcaaggga taaggcttcc ctaggtgtac aggggtggcc acttttgagg    4860
tggccgaagc cttgcaggat acaccctatc tgctgctcac tcttcttcgt ccaccagaaa    4920
ggagcagtgg gacagatgga cagggtcctt ccatgctaca gttccttgct tcttggagac    4980
tgggccttac atcctgagag agcccaggcc caggggatgg atgggtgt gagggctggt    5040 ggttaatggt ggaactttct ctgaagctcc tttctccctt gctattggtc cctatctccc    5100
gagcaagcct accctaaacc cccagagtgc acccaatgac cccctcccctt ggggtgactc    5160 ctgatgaagc acaactcccc gcaggccccc aacccactgc agtggccata tttgggcagt    5220
tcccagtcct gtgggctggg ctatctgggg agcagatgtg gggtctgggg ctccctgagg    5280
agtgggtcct gggtttggat cttttccctag ggggtcctct taccctctc ttcctcccct    5340 attgctgtaa atatttcaac aaaatggaaa aggaaaaaaa aaagacaaaa a             5391
```

<210> SEQ ID NO 3
<211> LENGTH: 11
<212> TYPE: PRT
<213> ORGANISM: bovine

<400> SEQUENCE: 3

```
Leu Met Glu Gln Leu Leu Asp Ile Leu Asp Ala
 1               5                  10
```

<210> SEQ ID NO 4
<211> LENGTH: 12
<212> TYPE: PRT
<213> ORGANISM: bovine

<400> SEQUENCE: 4

Gly Ile Ala Leu Phe Gln Tyr Leu Pro Ala Leu Gly
 1               5                  10

<210> SEQ ID NO 5
<211> LENGTH: 12
<212> TYPE: PRT
<213> ORGANISM: bovine

<400> SEQUENCE: 5

Thr Asp Gly Ser Thr Glu Met Leu Ser Gly Val Asp
 1               5                  10

<210> SEQ ID NO 6
<211> LENGTH: 10
<212> TYPE: PRT
<213> ORGANISM: bovine

<400> SEQUENCE: 6

Ile Tyr Val Met Pro Cys Ile Pro Tyr Arg
 1               5                  10

<210> SEQ ID NO 7
<211> LENGTH: 11
<212> TYPE: PRT
<213> ORGANISM: bovine

<400> SEQUENCE: 7

Ser Leu Gln Leu Tyr Val Ile Asn Ala Glu Val
 1               5                  10

<210> SEQ ID NO 8
<211> LENGTH: 12
<212> TYPE: PRT
<213> ORGANISM: bovine
<220> FEATURE:
<221> NAME/KEY: SITE
<222> LOCATION: (6)
<223> OTHER INFORMATION: Unkown

<400> SEQUENCE: 8

Ser Gly Asp Asn Ala Xaa Asn Ile Ala Ser Glu Leu
 1               5                  10

<210> SEQ ID NO 9
<211> LENGTH: 10
<212> TYPE: PRT
<213> ORGANISM: bovine

<400> SEQUENCE: 9

Val Pro Val Thr Pro Gly Asn Leu Gln Lys
 1               5                  10

<210> SEQ ID NO 10
<211> LENGTH: 11
<212> TYPE: PRT
<213> ORGANISM: bovine

<400> SEQUENCE: 10

Tyr Glu Gly Asn Trp Glu Thr Gly Tyr Asp Lys
 1               5                  10

```
<210> SEQ ID NO 11
<211> LENGTH: 17
<212> TYPE: PRT
<213> ORGANISM: bovine

<400> SEQUENCE: 11

Val Phe Leu Met Asp Pro Val Ile Phe Thr Val Ala His Leu Glu Ala
 1               5                  10                  15
Lys

<210> SEQ ID NO 12
<211> LENGTH: 11
<212> TYPE: PRT
<213> ORGANISM: bovine
<220> FEATURE:
<221> NAME/KEY: SITE
<222> LOCATION: (1)..(2)
<223> OTHER INFORMATION: Unknow.

<400> SEQUENCE: 12

Xaa Xaa Phe Ala Val Leu Met Ala His Arg Glu
 1               5                  10

<210> SEQ ID NO 13
<211> LENGTH: 207
<212> TYPE: PRT
<213> ORGANISM: Homo sapiens

<400> SEQUENCE: 13

Leu Tyr Tyr Leu Ala Ile Val Gly His Ser Leu Ser Ile Phe Thr Leu
 1               5                  10                  15

Val Ile Ser Leu Gly Ile Phe Val Phe Arg Ser Leu Gly Cys Gln Arg
                20                  25                  30

Val Thr Leu His Lys Asn Met Phe Leu Thr Tyr Ile Leu Asn Ser Met
            35                  40                  45

Ile Ile Ile Ile His Leu Pro Val Ser Cys Lys Ile Leu His Phe Phe
        50                  55                  60

His Gln Tyr Met Met Ala Cys Asn Tyr Phe Trp Met Leu Cys Glu Gly
 65                  70                  75                  80

Ile Tyr Leu His Thr Leu Ile Val Val Ala Val Phe Thr Glu Lys Gln
                85                  90                  95

Arg Leu Arg Trp Tyr Tyr Leu Leu Gly Trp Gly Phe Pro Leu Val Pro
                100                 105                 110

Thr Thr Ile His Ala Ile Thr Asp Asn Cys Trp Leu Ser Val Glu Thr
            115                 120                 125

His Leu Leu Tyr Ile Ile His Gly Pro Val Met Ala Ala Leu Val Val
        130                 135                 140

Asn Phe Phe Phe Leu Leu Asn Ile Val Leu Lys Ala Val Lys Ala Thr
145                 150                 155                 160

Met Ile Leu Val Pro Leu Leu Gly Ile Gln Phe Val Val Phe Pro Trp
                165                 170                 175

Tyr Val Met His Ser Leu Ile His Phe Gln Gly Phe Phe Val Ala Thr
                180                 185                 190

Ile Tyr Cys Phe Cys Asn Asn Glu Val Gln Thr Thr Val Lys Arg
                195                 200                 205

<210> SEQ ID NO 14
<211> LENGTH: 207
```

```
<212> TYPE: PRT
<213> ORGANISM: Mouse

<400> SEQUENCE: 14

Ser Tyr Tyr Leu Ala Leu Val Gly His Ser Met Ser Ile Ala Ala Leu
 1               5                  10                  15

Ile Ala Ser Met Gly Ile Phe Leu Phe Lys Asn Leu Ser Cys Gln Arg
            20                  25                  30

Val Thr Leu His Lys Asn Met Phe Leu Thr Tyr Ile Leu Asn Ser Ile
        35                  40                  45

Ile Ile Ile Ile His Leu Pro Ile Ser Cys Lys Ile Leu His Phe Phe
50                  55                  60

His Gln Tyr Met Met Ala Cys Asn Tyr Phe Trp Met Leu Cys Glu Gly
65                  70                  75                  80

Ile Tyr Leu His Thr Leu Ile Val Met Ala Val Phe Thr Glu Asp Gln
                85                  90                  95

Arg Leu Arg Trp Tyr Tyr Leu Leu Gly Trp Gly Phe Pro Ile Val Pro
            100                 105                 110

Thr Ile Ile His Ala Ile Thr Asp Asn Cys Trp Leu Ser Thr Glu Thr
        115                 120                 125

His Leu Leu Tyr Ile Ile His Gly Pro Val Met Ala Ala Leu Val Val
130                 135                 140

Asn Phe Phe Leu Leu Asn Ile Val Leu Lys Ala Val Lys Ala Thr
145                 150                 155                 160

Met Val Leu Val Pro Leu Leu Gly Ile Gln Phe Val Val Phe Pro Trp
                165                 170                 175

Tyr Leu Met His Ser Leu Ile His Phe Gln Gly Phe Phe Val Ala Thr
            180                 185                 190

Ile Tyr Cys Phe Cys Asn His Glu Val Gln Val Thr Leu Lys Arg
        195                 200                 205

<210> SEQ ID NO 15
<211> LENGTH: 207
<212> TYPE: PRT
<213> ORGANISM: Mouse

<400> SEQUENCE: 15

Leu Phe Tyr Leu Thr Ile Ile Gly His Gly Leu Ser Ile Ala Ser Leu
 1               5                  10                  15

Ile Ile Ser Leu Ile Ile Phe Phe Lys Ser Leu Ser Cys Gln Arg
            20                  25                  30

Ile Thr Leu His Lys Asn Leu Phe Phe Ser Phe Val Cys Asn Ser Ile
        35                  40                  45

Val Thr Ile Ile His Leu Pro Val Ser Cys Lys Val Ser Gln Phe Ile
        50                  55                  60

His Leu Tyr Leu Met Gly Cys Asn Tyr Phe Trp Met Leu Cys Glu Gly
65                  70                  75                  80

Ile Tyr Leu His Thr Leu Ile Val Val Ala Val Phe Ala Glu Lys Gln
                85                  90                  95

His Leu Met Trp Tyr Tyr Phe Leu Gly Trp Gly Phe Pro Leu Leu Pro
            100                 105                 110

Ala Cys Ile His Ala Ile Ala Asp Asn Cys Trp Ile Ser Ser Asp Thr
        115                 120                 125

His Leu Leu Tyr Ile Ile His Gly Pro Ile Cys Ala Ala Leu Leu Val
130                 135                 140
```

-continued

Asn Leu Phe Phe Leu Leu Asn Ile Val Met Lys Ala Val Arg Ala Thr
145                 150                 155                 160

Leu Ile Leu Val Pro Leu Leu Gly Ile Glu Phe Val Leu Phe Pro Trp
                165                 170                 175

Tyr Val Met His Ile Leu Met His Tyr Gln Gly Leu Leu Val Ser Thr
            180                 185                 190

Ile Phe Cys Phe Phe Asn Gly Glu Val Gln Ala Ile Leu Arg Arg
        195                 200                 205

<210> SEQ ID NO 16
<211> LENGTH: 207
<212> TYPE: PRT
<213> ORGANISM: Mouse

<400> SEQUENCE: 16

Ala Leu Ile Val Asn Tyr Leu Gly His Cys Val Ser Val Val Ala Leu
1               5                   10                  15

Val Ala Ala Phe Leu Leu Phe Leu Leu Arg Ser Ile Arg Cys Leu Arg
                20                  25                  30

Asn Val Ile His Trp Asn Leu Ile Thr Thr Phe Ile Leu Arg Asn Ile
            35                  40                  45

Ala Trp Phe Leu Leu Gln Glu Val Trp Cys Arg Cys Ile Thr Thr Ile
        50                  55                  60

Phe Asn Tyr Phe Val Val Thr Asn Phe Phe Trp Met Phe Val Glu Gly
65                  70                  75                  80

Cys Tyr Leu His Thr Ala Ile Val Met Thr Tyr Ser Thr Glu His Leu
                85                  90                  95

Arg Lys Trp Leu Phe Leu Phe Ile Gly Trp Cys Ile Pro Cys Pro Ile
            100                 105                 110

Ile Ile Ala Trp Ala Val Gly Glu Gln Cys Trp Phe Gly Lys Glu Ala
        115                 120                 125

Gly Asp Leu Tyr Ile Tyr Gln Gly Pro Val Met Leu Val Leu Leu Ile
130                 135                 140

Asn Phe Val Phe Leu Phe Asn Ile Val Arg Lys Ala Val Lys Ala Thr
145                 150                 155                 160

Leu Val Leu Leu Pro Leu Leu Gly Ile Thr Tyr Met Leu Phe Phe Val
                165                 170                 175

Tyr Phe Asn Ser Phe Leu Gln Ser Phe Gln Gly Phe Phe Val Ser Val
            180                 185                 190

Phe Tyr Cys Phe Phe Asn Gly Glu Val Arg Ala Ala Leu Arg Asn
        195                 200                 205

<210> SEQ ID NO 17
<211> LENGTH: 207
<212> TYPE: PRT
<213> ORGANISM: Mouse

<400> SEQUENCE: 17

Ala Leu Ile Ile Asn Tyr Leu Gly His Cys Val Ser Val Val Ala Leu
1               5                   10                  15

Val Ala Ala Phe Leu Leu Phe Leu Leu Arg Ser Ile Arg Cys Leu Arg
                20                  25                  30

Asn Val Ile His Trp Asn Leu Ile Thr Thr Phe Ile Leu Arg Asn Ile
            35                  40                  45

Thr Trp Phe Leu Leu Gln Glu Val Trp Cys Arg Cys Val Thr Thr Ile
        50                  55                  60

```
Phe Asn Tyr Phe Val Val Thr Asn Phe Phe Trp Met Phe Val Glu Gly
 65                  70                  75                  80

Cys Tyr Leu His Thr Ala Ile Val Met Thr Tyr Ser Thr Glu His Leu
                 85                  90                  95

Arg Lys Trp Leu Phe Leu Phe Ile Gly Trp Cys Ile Pro Cys Pro Ile
            100                 105                 110

Ile Val Ala Trp Ala Val Gly Glu Gln Cys Trp Phe Gly Lys Glu Pro
        115                 120                 125

Gly Asp Leu Tyr Ile Tyr Gln Gly Pro Ile Ile Leu Val Leu Leu Ile
    130                 135                 140

Asn Phe Val Phe Leu Phe Asn Ile Val Arg Lys Ala Val Lys Ala Thr
145                 150                 155                 160

Leu Val Leu Leu Pro Leu Leu Gly Ile Thr Tyr Met Leu Phe Phe Val
                165                 170                 175

Tyr Phe Asn Ser Phe Leu Gln Ser Phe Gln Gly Phe Phe Val Ser Val
            180                 185                 190

Phe Tyr Cys Phe Phe Asn Gly Glu Val Arg Ser Ala Leu Arg Lys
        195                 200                 205

<210> SEQ ID NO 18
<211> LENGTH: 207
<212> TYPE: PRT
<213> ORGANISM: Homo sapiens

<400> SEQUENCE: 18

Ala Val Ile Ile Asn Tyr Leu Gly His Cys Ile Ser Leu Val Ala Leu
  1               5                  10                  15

Leu Val Ala Phe Val Leu Phe Leu Leu Arg Ser Ile Arg Cys Leu Arg
             20                  25                  30

Asn Ile Ile His Trp Asn Leu Ile Ser Ala Phe Ile Leu Arg Asn Ala
         35                  40                  45

Thr Trp Phe Val Val Gln Val Gly Trp Cys Arg Leu Val Thr Ala Ala
     50                  55                  60

Tyr Asn Tyr Phe His Val Thr Asn Phe Phe Trp Met Phe Gly Glu Gly
 65                  70                  75                  80

Cys Tyr Leu His Thr Ala Ile Val Leu Thr Tyr Ser Thr Asp Arg Leu
                 85                  90                  95

Arg Lys Trp Met Phe Ile Cys Ile Gly Trp Gly Val Pro Phe Pro Ile
            100                 105                 110

Ile Val Ala Trp Ala Ile Gly Glu Lys Cys Trp Phe Gly Lys Arg Pro
        115                 120                 125

Gly Val Tyr Tyr Ile Tyr Gln Gly Pro Met Ile Leu Val Leu Leu Ile
    130                 135                 140

Asn Phe Ile Phe Leu Phe Asn Ile Val Arg Lys Ala Val Lys Ala Thr
145                 150                 155                 160

Leu Val Leu Leu Pro Leu Leu Gly Ile Thr Tyr Met Leu Phe Phe Val
                165                 170                 175

Tyr Phe Asn Ser Phe Leu Glu Ser Phe Gln Gly Phe Phe Val Ser Val
            180                 185                 190

Phe Tyr Cys Phe Leu Asn Ser Glu Val Arg Ser Ala Ile Arg Lys
        195                 200                 205

<210> SEQ ID NO 19
<211> LENGTH: 207
<212> TYPE: PRT
<213> ORGANISM: Manduca (tobacco hornworm-insect)
```

```
<400> SEQUENCE: 19

Ala Ser Leu Ile Tyr Leu Ala Gly Tyr Ser Leu Ser Leu Ala Val Leu
  1               5                  10                  15

Ser Leu Ala Val Phe Val Phe Leu Phe Lys Asp Leu Arg Cys Leu Arg
             20                  25                  30

Asn Thr Ile His Thr Asn Leu Met Ser Thr Tyr Ile Leu Ser Ala Cys
             35                  40                  45

Ser Trp Ile Leu Asn Leu Gln Thr Ser Cys Met Ile Leu Val Ile Cys
         50                  55                  60

Met Asn Tyr Phe Tyr Leu Thr Asn Phe Phe Trp Met Leu Val Glu Gly
 65                  70                  75                  80

Leu Tyr Leu Tyr Met Leu Val Val Glu Thr Phe Thr Ala Glu Asn Ile
                 85                  90                  95

Lys Leu Lys Val Tyr Thr Thr Ile Gly Trp Gly Ala Pro Ala Val Phe
                100                 105                 110

Ile Thr Ile Trp Val Ile Ser Lys Met Cys Ile Trp Met His Glu His
            115                 120                 125

Gln Val Asp Trp Ile His Lys Ala Pro Ala Leu Val Gly Leu Ala Leu
        130                 135                 140

Asn Leu Phe Phe Leu Ile Arg Ile Met Arg Lys Ala Thr Lys Ala Leu
145                 150                 155                 160

Leu Val Leu Ile Pro Leu Leu Gly Ile Thr Asn Leu Val Leu Cys
                165                 170                 175

Tyr Thr Arg Ala Leu Met Leu Ser Thr Gln Gly Phe Thr Val Ala Leu
                180                 185                 190

Phe Tyr Cys Phe Met Asn Thr Glu Val Arg His Ala Ile Arg Tyr
            195                 200                 205

<210> SEQ ID NO 20
<211> LENGTH: 207
<212> TYPE: PRT
<213> ORGANISM: rat

<400> SEQUENCE: 20

Leu Ser Val Ile Thr Trp Val Gly Ile Val Ser Leu Val Cys Leu
  1               5                  10                  15

Ala Ile Cys Ile Ser Thr Phe Cys Leu Arg Gly Leu Gln Thr Asp Arg
             20                  25                  30

Asn Thr Ile His Lys Asn Leu Cys Ile Asn Leu Phe Leu Ala Glu Leu
             35                  40                  45

Leu Phe Leu Val Gly Ile Glu Val Ala Cys Pro Ile Phe Ala Gly Leu
         50                  55                  60

Leu His Tyr Phe Phe Leu Ala Ala Phe Ser Trp Leu Cys Leu Glu Gly
 65                  70                  75                  80

Val His Leu Tyr Leu Leu Val Glu Val Phe Glu Ser Glu Tyr Ser
                 85                  90                  95

Arg Thr Lys Tyr Tyr Tyr Leu Gly Gly Tyr Cys Phe Pro Ala Leu Val
                100                 105                 110

Val Gly Ile Ala Ala Ala Ile Lys Ala Cys Trp Leu Arg Val Asp Asn
            115                 120                 125

Tyr Phe Ile Trp Ser Phe Ile Gly Pro Val Ser Phe Val Ile Val Val
        130                 135                 140

Asn Leu Val Phe Leu Met Val Thr Leu Lys Ser Trp Ala Leu Gly Ala
145                 150                 155                 160
```

```
Ile Ala Leu Leu Phe Leu Leu Gly Leu Thr Trp Ala Phe Gly Leu Leu
                165                 170                 175

Tyr Leu Phe Thr Thr Phe Asn Ala Phe Gln Gly Val Phe Ile Phe Val
            180                 185                 190

Phe His Cys Ala Leu Gln Lys Lys Val His Lys Glu Tyr Ser Lys
        195                 200                 205

<210> SEQ ID NO 21
<211> LENGTH: 207
<212> TYPE: PRT
<213> ORGANISM: Homo sapiens

<400> SEQUENCE: 21

Leu Thr Leu Ile Thr Arg Val Gly Leu Ala Leu Ser Leu Phe Cys Leu
 1               5                  10                  15

Leu Leu Cys Ile Leu Thr Phe Leu Val Arg Pro Ile Gln Gly Ser Arg
            20                  25                  30

Thr Thr Ile His Leu His Leu Cys Ile Cys Leu Phe Val Gly Ser Thr
        35                  40                  45

Ile Phe Leu Ala Gly Ile Gly Leu Arg Cys Arg Leu Val Ala Gly Leu
    50                  55                  60

Leu His Tyr Cys Phe Leu Ala Ala Phe Cys Trp Met Ser Leu Glu Gly
65                  70                  75                  80

Leu Glu Leu Tyr Phe Leu Val Val Arg Val Phe Gln Gly Gln Gly Leu
                85                  90                  95

Ser Thr Arg Trp Leu Cys Leu Ile Gly Tyr Gly Val Pro Leu Leu Ile
            100                 105                 110

Val Gly Val Ser Ala Ala Ile Arg Tyr Cys Trp Leu Asp Phe Glu Gln
        115                 120                 125

Gly Phe Leu Trp Ser Phe Leu Gly Pro Val Thr Phe Ile Ile Leu Cys
    130                 135                 140

Asn Ala Val Ile Phe Val Thr Thr Val Arg Ala Leu Thr Ile Thr Ala
145                 150                 155                 160

Ile Ala Gln Leu Phe Leu Leu Gly Cys Thr Trp Val Phe Gly Leu Phe
                165                 170                 175

Tyr Val Phe Thr Ile Leu Asn Cys Leu Gln Gly Ala Phe Leu Tyr Leu
            180                 185                 190

Leu His Cys Leu Leu Asn Lys Lys Val Arg Glu Glu Tyr Arg Lys
        195                 200                 205

<210> SEQ ID NO 22
<211> LENGTH: 207
<212> TYPE: PRT
<213> ORGANISM: mouse

<400> SEQUENCE: 22

Leu Tyr Ile Ile Ser His Val Gly Ile Ile Ser Leu Val Cys Leu
 1               5                  10                  15

Val Leu Ala Ile Ala Thr Phe Leu Cys Arg Ser Ile Arg Asn His Asn
            20                  25                  30

Thr Tyr Leu His Leu His Leu Cys Val Cys Leu Leu Leu Ala Lys Thr
        35                  40                  45

Leu Phe Leu Ala Gly Ile Lys Thr Gly Cys Ala Ile Ile Ala Gly Phe
    50                  55                  60

Leu His Tyr Leu Phe Leu Ala Cys Phe Phe Trp Met Leu Val Glu Ala
65                  70                  75                  80
```

```
Val Ile Leu Phe Leu Met Val Val Asn Tyr Phe Ser Ser Arg Asn Ile
                85                  90                  95

Lys Met Leu His Ile Cys Ala Phe Gly Tyr Gly Leu Pro Met Leu Val
            100                 105                 110

Val Val Ile Ser Ala Ser Val Asn Arg Cys Trp Leu Asn Thr Glu Thr
        115                 120                 125

Gly Phe Ile Trp Ser Phe Leu Gly Pro Val Cys Thr Val Ile Val Ile
    130                 135                 140

Asn Ser Leu Leu Leu Thr Trp Thr Leu Arg Leu Leu Thr Phe Lys Ala
145                 150                 155                 160

Phe Ala Gln Leu Phe Ile Leu Gly Cys Ser Trp Val Leu Gly Ile Phe
                165                 170                 175

Tyr Leu Phe Thr Ile Ile Asn Ser Leu Gln Gly Ala Phe Ile Phe Leu
                180                 185                 190

Ile His Cys Leu Leu Asn Gly Gln Val Arg Glu Glu Tyr Lys Arg
                195                 200                 205

<210> SEQ ID NO 23
<211> LENGTH: 207
<212> TYPE: PRT
<213> ORGANISM: mouse

<400> SEQUENCE: 23

Leu Tyr Ile Ile Ser His Val Gly Thr Val Ile Ser Leu Val Cys Leu
1               5                   10                  15

Ala Leu Ala Ile Ala Thr Phe Leu Cys Arg Ala Val Gln Asn His Asn
                20                  25                  30

Thr Tyr Met His Leu His Leu Cys Val Cys Leu Phe Leu Ala Lys Ile
            35                  40                  45

Leu Phe Leu Thr Gly Ile Gln Thr Ala Cys Ala Ile Ile Ala Gly Phe
    50                  55                  60

Leu His Tyr Leu Phe Leu Ala Cys Phe Phe Trp Met Leu Val Glu Ala
65                  70                  75                  80

Val Met Leu Phe Leu Met Val Val Asn Tyr Phe Ser Ser Arg Asn Ile
                85                  90                  95

Lys Met Leu His Leu Cys Ala Phe Gly Tyr Gly Leu Pro Val Leu Val
            100                 105                 110

Val Ile Ile Ser Ala Ser Val Asn Arg Cys Trp Leu Asn Thr Glu Thr
        115                 120                 125

Gly Phe Ile Trp Ser Phe Leu Gly Pro Val Cys Met Ile Thr Ile
    130                 135                 140

Asn Ser Val Leu Leu Ala Trp Thr Leu Arg Leu Leu Thr Phe Lys Ala
145                 150                 155                 160

Ile Ala Gln Ile Phe Ile Leu Gly Cys Ser Trp Val Leu Gly Ile Phe
                165                 170                 175

Tyr Leu Phe Thr Ile Ile Asn Ser Leu Gln Gly Ala Phe Ile Phe Leu
                180                 185                 190

Ile His Cys Leu Leu Asn Arg Gln Val Arg Asp Glu Tyr Lys Lys
                195                 200                 205

<210> SEQ ID NO 24
<211> LENGTH: 207
<212> TYPE: PRT
<213> ORGANISM: Homo sapiens

<400> SEQUENCE: 24
```

```
Leu Gln Val Met Tyr Thr Val Gly Tyr Ser Leu Ser Leu Ala Thr Leu
 1               5                  10                  15

Leu Leu Ala Leu Leu Ile Leu Ser Phe Arg Arg Leu His Cys Thr Arg
            20                  25                  30

Asn Tyr Ile His Ile Asn Leu Phe Thr Ser Phe Met Leu Arg Ala Ala
            35                  40                  45

Ala Ile Leu Ser Arg Asp Leu Ala Ala Cys Arg Thr Ala Gln Ile Val
        50                  55                  60

Thr Gln Tyr Cys Val Gly Ala Asn Tyr Thr Trp Leu Leu Val Glu Gly
 65                  70                  75                  80

Val Tyr Leu His Ser Leu Leu Val Leu Val Gly Gly Ser Glu Glu Gly
                85                  90                  95

His Phe Arg Tyr Tyr Leu Leu Gly Trp Gly Ala Pro Ala Leu Phe
                100                 105                 110

Val Ile Pro Trp Val Ile Val Thr Gln Cys Trp Glu Arg Asn Glu Val
            115                 120                 125

Lys Ala Ile Trp Ile Ile Arg Thr Pro Ile Leu Met Thr Ile Leu Ile
    130                 135                 140

Asn Phe Leu Ile Phe Ile Arg Ile Leu Leu Arg Leu Ala Arg Ser Thr
145                 150                 155                 160

Leu Thr Leu Val Pro Leu Leu Gly Val His Glu Val Val Phe Ala Pro
                165                 170                 175

Gly Phe Glu Ile Phe Leu Ser Ser Phe Gln Gly Phe Leu Val Ser Val
                180                 185                 190

Leu Tyr Cys Phe Ile Asn Lys Glu Val Gln Ser Glu Ile Arg Arg
            195                 200                 205

<210> SEQ ID NO 25
<211> LENGTH: 207
<212> TYPE: PRT
<213> ORGANISM: rat

<400> SEQUENCE: 25

Tyr Gln Val Met Tyr Thr Val Gly Tyr Ser Leu Ser Leu Gly Ala Leu
 1               5                  10                  15

Leu Leu Ala Leu Val Ile Leu Leu Arg Lys Leu His Cys Thr Arg
            20                  25                  30

Asn Tyr Ile His Gly Asn Leu Phe Ala Ser Phe Val Leu Lys Ala Gly
            35                  40                  45

Ser Val Leu Val Ile Asp Val Ala Gly Cys Arg Val Ala Thr Val Ile
        50                  55                  60

Met Gln Tyr Gly Ile Ile Ala Asn Tyr Cys Trp Leu Leu Val Glu Gly
 65                  70                  75                  80

Val Tyr Leu Tyr Ser Leu Leu Ser Ile Thr Thr Phe Ser Glu Lys Ser
                85                  90                  95

Phe Phe Ser Leu Tyr Leu Cys Ile Gly Trp Gly Ser Pro Leu Leu Phe
                100                 105                 110

Val Ile Pro Trp Val Val Val Gln Cys Trp Thr Ser Asn Asp Asn
            115                 120                 125

Met Gly Phe Trp Ile Leu Arg Ile Pro Val Leu Leu Ala Ile Leu Ile
    130                 135                 140

Asn Phe Ile Phe Ala Arg Ile Ile Phe Arg Leu Ala Arg Ser Thr
145                 150                 155                 160

Leu Thr Leu Ile Pro Leu Leu Gly Val His Glu Val Val Phe Ala Phe
                165                 170                 175
```

```
Phe Phe Asp Leu Phe Phe Ser Ser Phe Gln Gly Leu Leu Val Ala Val
                180                 185                 190

Leu Tyr Cys Phe Leu Asn Lys Glu Val Gln Ala Glu Leu Leu Arg
            195                 200                 205

<210> SEQ ID NO 26
<211> LENGTH: 207
<212> TYPE: PRT
<213> ORGANISM: bovine

<400> SEQUENCE: 26

Val Lys Ala Leu Tyr Thr Val Gly Tyr Ser Thr Ser Leu Val Thr Leu
  1               5                  10                  15

Thr Thr Ala Met Val Ile Leu Cys Phe Arg Lys Leu His Cys Thr Arg
                20                  25                  30

Asn Phe Ile His Met Asn Leu Phe Val Ser Phe Met Leu Arg Ala Ile
                35                  40                  45

Ser Val Phe Ile Lys Asp Thr Val Glu Cys Lys Ala Val Met Val Phe
 50                  55                  60

Phe His Tyr Cys Val Val Ser Asn Tyr Phe Trp Leu Phe Ile Glu Gly
 65                  70                  75                  80

Leu Tyr Leu Phe Thr Leu Leu Val Glu Thr Phe Phe Pro Glu Arg Arg
                85                  90                  95

Tyr Phe Tyr Trp Tyr Ile Ile Ile Gly Trp Gly Thr Pro Thr Val Cys
                100                 105                 110

Val Ser Val Trp Ala Met Leu Thr Gly Cys Trp Asp Met Asn Asp Asn
                115                 120                 125

Thr Ala Leu Trp Val Ile Lys Gly Pro Val Val Gly Ser Ile Met Val
130                 135                 140

Asn Phe Val Leu Phe Ile Gly Ile Ile Leu Arg Leu Ala Arg Ser Thr
145                 150                 155                 160

Leu Leu Leu Ile Pro Leu Phe Gly Ile His Tyr Thr Val Phe Ala Phe
                165                 170                 175

Val Phe Glu Leu Gly Leu Gly Ser Phe Gln Gly Phe Val Val Ala Val
                180                 185                 190

Leu Tyr Cys Phe Leu Asn Gly Glu Val Gln Ala Glu Ile Lys Arg
            195                 200                 205

<210> SEQ ID NO 27
<211> LENGTH: 207
<212> TYPE: PRT
<213> ORGANISM: Homo sapiens

<400> SEQUENCE: 27

Val Lys Ala Ile Tyr Thr Leu Gly Tyr Ser Val Ser Leu Met Ser Leu
  1               5                  10                  15

Ala Thr Gly Ser Ile Ile Leu Cys Phe Arg Lys Leu His Cys Thr Arg
                20                  25                  30

Asn Tyr Ile His His Leu Asn Leu Phe Leu Ser Phe Ile Leu Arg Ala Ile
                35                  40                  45

Ser Val Leu Val Lys Asp Trp Val Gly Cys Lys Leu Ser Leu Val Phe
 50                  55                  60

Leu Gln Tyr Cys Ile Met Ala Asn Phe Phe Trp Leu Leu Val Glu Gly
 65                  70                  75                  80

Leu Tyr Leu His His Thr Leu Leu Val Ala Ala Met Leu Pro Pro Arg Arg
                85                  90                  95
```

```
Cys Phe Leu Ala Tyr Leu Leu Ile Gly Trp Gly Leu Pro Thr Val Cys
            100                 105                 110

Ile Gly Ala Trp Thr Ala Ala Thr Gly Cys Trp Asp Thr Asn Asp His
            115                 120                 125

Ser Val Pro Trp Val Ile Arg Ile Pro Ile Leu Ile Ser Ile Ile Val
            130                 135                 140

Asn Phe Val Leu Phe Ile Ser Ile Lys Arg Leu Ala Lys Ser Thr
145                 150                 155                 160

Leu Leu Leu Ile Pro Leu Phe Gly Val His Tyr Met Val Phe Ala Val
                165                 170                 175

Leu Phe Glu Leu Cys Leu Gly Ser Phe Gln Gly Leu Val Val Ala Val
            180                 185                 190

Leu Tyr Cys Phe Leu Asn Ser Glu Val Gln Cys Glu Leu Lys Arg
        195                 200                 205
```

<210> SEQ ID NO 28
<211> LENGTH: 207
<212> TYPE: PRT
<213> ORGANISM: rat

<400> SEQUENCE: 28

```
Val Lys Ile Ile Tyr Thr Thr Gly His Ser Ile Ser Ile Val Ala Leu
1               5                   10                  15

Cys Val Ala Ile Ala Ile Leu Val Leu Arg Arg Leu His Cys Pro Arg
            20                  25                  30

Asn Tyr Ile His Thr Gln Leu Phe Ala Thr Phe Ile Leu Lys Ala Ser
            35                  40                  45

Ala Val Phe Leu Lys Asp Thr Ile Leu Cys Lys Val Ser Val Ala Val
        50                  55                  60

Ser His Phe Ala Thr Met Thr Asn Phe Ser Trp Leu Leu Ala Glu Ala
65                  70                  75                  80

Val Tyr Leu Ser Cys Leu Leu Ala Ser Thr Ser Pro Arg Ser Lys Pro
                85                  90                  95

Ala Phe Trp Trp Leu Val Leu Ala Gly Trp Gly Leu Pro Val Leu Cys
            100                 105                 110

Thr Gly Thr Trp Val Gly Cys Thr Ala Cys Trp Asp Leu Asp Asp Ser
            115                 120                 125

Ser Pro Tyr Trp Ile Ile Lys Gly Pro Ile Val Leu Ser Val Gly Val
            130                 135                 140

Asn Phe Gly Leu Phe Leu Asn Ile Ile Trp Arg Leu Ser Lys Ser Thr
145                 150                 155                 160

Leu Leu Leu Ile Pro Leu Phe Gly Ile His Tyr Ile Ile Phe Asn Phe
                165                 170                 175

Pro Leu Glu Leu Gly Leu Gly Ser Phe Gln Gly Phe Val Val Ala Val
            180                 185                 190

Leu Tyr Cys Phe Leu Asn Gln Glu Val Arg Thr Glu Ile Ser Arg
        195                 200                 205
```

<210> SEQ ID NO 29
<211> LENGTH: 207
<212> TYPE: PRT
<213> ORGANISM: Homo sapiens

<400> SEQUENCE: 29

```
Val Lys Thr Gly Tyr Thr Ile Gly Tyr Gly Leu Ser Leu Ala Thr Leu
1               5                   10                  15
```

-continued

```
Leu Val Ala Thr Ala Ile Leu Ser Phe Arg Lys Leu His Cys Thr Arg
                20                  25                  30
Asn Tyr Ile His Met His Leu Phe Ile Ser Phe Ile Leu Arg Ala Ala
            35                  40                  45
Ala Val Phe Ile Lys Asp Ser Val Gly Cys Lys Ala Ala Met Val Phe
        50                  55                  60
Phe Gln Tyr Cys Val Met Ala Asn Phe Phe Trp Leu Leu Val Glu Gly
 65                  70                  75                  80
Leu Tyr Leu Tyr Thr Leu Leu Ala Val Ser Phe Phe Ser Glu Arg Lys
                85                  90                  95
Tyr Phe Trp Gly Tyr Ile Leu Ile Gly Trp Gly Val Pro Ser Thr Phe
            100                 105                 110
Thr Met Val Trp Thr Ile Ala Tyr Gly Cys Trp Asp Thr Ile Asn Ser
        115                 120                 125
Ser Leu Trp Trp Ile Ile Lys Gly Pro Ile Leu Thr Ser Ile Leu Val
130                 135                 140
Asn Phe Ile Leu Phe Ile Cys Ile Ile Ser Arg Leu Ala Arg Ser Thr
145                 150                 155                 160
Leu Leu Leu Ile Pro Leu Phe Gly Val His Tyr Ile Met Phe Ala Phe
                165                 170                 175
Val Phe Glu Leu Val Val Gly Ser Phe Gln Gly Phe Val Val Ala Ile
            180                 185                 190
Leu Tyr Cys Phe Leu Asn Gly Glu Val Gln Ala Glu Leu Arg Arg
            195                 200                 205

<210> SEQ ID NO 30
<211> LENGTH: 207
<212> TYPE: PRT
<213> ORGANISM: rat

<400> SEQUENCE: 30

Leu Lys Val Met Tyr Thr Val Gly Tyr Ser Ser Ser Leu Ala Met Leu
  1               5                  10                  15
Leu Val Ala Leu Ser Ile Leu Cys Phe Arg Arg Leu His Cys Thr Arg
                20                  25                  30
Asn Tyr Ile His Met His Leu Phe Val Ser Phe Ile Leu Arg Ala Leu
            35                  40                  45
Ser Asn Phe Ile Lys Asp Lys Val Gly Cys Lys Leu Val Met Ile Phe
        50                  55                  60
Phe Gln Tyr Cys Ile Met Ala Asn Tyr Ala Trp Leu Leu Val Glu Gly
 65                  70                  75                  80
Leu Tyr Leu His Thr Leu Leu Ala Ile Ser Phe Phe Ser Glu Arg Lys
                85                  90                  95
Tyr Leu Gln Ala Phe Val Leu Leu Gly Trp Gly Ser Pro Ala Ile Phe
            100                 105                 110
Val Ala Leu Trp Ala Ile Thr Thr Gly Cys Trp Asp Ile Asn Ala Asn
        115                 120                 125
Ala Ser Val Trp Val Ile Arg Gly Pro Val Ile Leu Ser Ile Leu Ile
130                 135                 140
Asn Phe Ile Phe Phe Ile Asn Ile Leu Lys Arg Leu Ala Lys Ser Thr
145                 150                 155                 160
Leu Leu Leu Ile Pro Leu Phe Gly Ile His Tyr Ile Val Phe Ala Phe
                165                 170                 175
Phe Phe Glu Leu Ala Leu Gly Ser Phe Gln Gly Leu Val Val Ala Val
            180                 185                 190
```

```
Leu Tyr Cys Phe Leu Asn Gly Glu Val Gln Leu Glu Val Gln Lys
        195                 200                 205

<210> SEQ ID NO 31
<211> LENGTH: 207
<212> TYPE: PRT
<213> ORGANISM: Homo sapiens

<400> SEQUENCE: 31

Leu Gly Met Ile Tyr Thr Val Gly Tyr Ser Val Ser Leu Ala Ser Leu
  1               5                  10                  15

Thr Val Ala Val Leu Ile Leu Ala Phe Arg Arg Leu His Cys Thr Arg
             20                  25                  30

Asn Tyr Ile His Met His Leu Phe Leu Ser Phe Met Leu Arg Ala Val
         35                  40                  45

Ser Ile Phe Val Lys Asp Tyr Ala Gly Cys Arg Val Ala Val Thr Phe
     50                  55                  60

Phe Leu Tyr Phe Leu Ala Thr Asn Tyr Tyr Trp Ile Leu Val Glu Gly
 65                  70                  75                  80

Leu Tyr Leu His Ser Leu Ile Phe Met Ala Phe Phe Ser Glu Lys Lys
                 85                  90                  95

Tyr Leu Trp Gly Phe Thr Val Phe Gly Trp Gly Leu Pro Ala Val Phe
            100                 105                 110

Val Ala Val Trp Val Ser Val Thr Gly Cys Trp Asp Leu Ser Ser Gly
            115                 120                 125

Asn Lys Lys Trp Ile Ile Gln Val Pro Ile Leu Ala Ser Ile Val Leu
        130                 135                 140

Asn Phe Ile Leu Phe Ile Asn Ile Val Arg Lys Leu Leu Lys Ser Thr
145                 150                 155                 160

Leu Val Leu Met Pro Leu Phe Gly Val His Tyr Ile Val Phe Met Ala
                165                 170                 175

His Tyr Glu Met Leu Phe Asn Ser Phe Gln Gly Phe Phe Val Ala Ile
            180                 185                 190

Ile Tyr Cys Phe Cys Asn Gly Glu Val Gln Ala Glu Ile Asn Lys
        195                 200                 205
```